(12) United States Patent
Abraham et al.

(10) Patent No.: US 12,410,204 B2
(45) Date of Patent: Sep. 9, 2025

(54) CHIRAL SYNTHESIS OF A TERTIARY ALCOHOL

(71) Applicant: Recurium IP Holdings, LLC, San Diego, CA (US)

(72) Inventors: Sunny Abraham, San Diego, CA (US); Brant Clayton Boren, San Diego, CA (US); Sobhana Babu Boga, San Diego, CA (US); Aditya Krishnan Unni, San Diego, CA (US); Peter Qinhua Huang, San Diego, CA (US); Kevin Duane Bunker, Escondido, CA (US); Benjamin Anthony Pratt, Encinitas, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 686 days.

(21) Appl. No.: 17/756,011

(22) PCT Filed: Nov. 12, 2020

(86) PCT No.: PCT/US2020/060298
§ 371 (c)(1),
(2) Date: May 13, 2022

(87) PCT Pub. No.: WO2021/097139
PCT Pub. Date: May 20, 2021

(65) Prior Publication Data
US 2023/0002426 A1   Jan. 5, 2023

Related U.S. Application Data

(60) Provisional application No. 63/037,761, filed on Jun. 11, 2020, provisional application No. 62/935,894, filed on Nov. 15, 2019.

(51) Int. Cl.
*C07F 9/59* (2006.01)
*C07F 9/572* (2006.01)

(52) U.S. Cl.
CPC .............. *C07F 9/59* (2013.01); *C07F 9/572* (2013.01); *C07B 2200/13* (2013.01)

(58) Field of Classification Search
CPC ......... C07F 9/59; C07F 9/572; C07B 2200/13
See application file for complete search history.

(56) References Cited

U.S. PATENT DOCUMENTS

| | | | |
|---|---|---|---|
| 6,998,491 B2 | 2/2006 | Ishi et al. | |
| 8,198,445 B2 * | 6/2012 | Ishihara | B01J 31/1815 548/413 |
| 8,624,024 B2 | 1/2014 | Ishihara et al. | |
| 11,124,518 B2 | 9/2021 | Huang et al. | |
| 11,261,192 B2 | 3/2022 | Huang et al. | |
| 2010/0113786 A1 | 5/2010 | Ishihara et al. | |
| 2020/0157112 A1 | 5/2020 | Huang et al. | |
| 2021/0139482 A1 | 5/2021 | Huang et al. | |
| 2021/0317124 A1 | 10/2021 | Huang et al. | |
| 2022/0024939 A1 | 1/2022 | Huang et al. | |
| 2023/0008362 A1 | 1/2023 | Samatar et al. | |
| 2023/0054854 A1 | 2/2023 | Samatar et al. | |
| 2023/0068370 A1 | 3/2023 | Samatar et al. | |
| 2023/0087941 A1 | 3/2023 | Samatar et al. | |
| 2023/0210854 A1 | 7/2023 | Samatar et al. | |
| 2023/0234956 A1 | 7/2023 | Huang et al. | |
| 2023/0265097 A1 | 8/2023 | Hopkins et al. | |
| 2024/0197743 A1 | 6/2024 | Pultar et al. | |
| 2024/0261295 A1 | 8/2024 | Donate et al. | |
| 2024/0299395 A1 | 9/2024 | Donate et al. | |
| 2024/0325397 A1 | 10/2024 | Samatar et al. | |
| 2024/0325412 A1 | 10/2024 | Donate et al. | |
| 2024/0335447 A1 | 10/2024 | Donate et al. | |
| 2024/0391924 A1 | 11/2024 | Huang et al. | |
| 2024/0408097 A1 | 12/2024 | Samatar et al. | |

FOREIGN PATENT DOCUMENTS

| | | |
|---|---|---|
| CN | 101641364 A | 2/2010 |
| CN | 103012061 A | 4/2013 |
| EP | 2128167 | 12/2009 |
| WO | WO 2008/111371 A1 | 9/2008 |
| WO | WO 2009/110609 | 9/2009 |
| WO | WO 2019/028008 | 2/2019 |
| WO | WO 2019/173082 | 9/2019 |
| WO | WO 2020/210320 | 10/2020 |
| WO | WO 2021/097139 | 5/2021 |
| WO | WO 2021/127039 | 6/2021 |
| WO | WO 2021/127044 | 6/2021 |
| WO | WO 2021/127045 | 6/2021 |
| WO | WO 2021/127047 | 6/2021 |
| WO | WO 2021/231653 | 11/2021 |
| WO | WO 2021/252667 | 12/2021 |
| WO | WO 2022/011391 | 1/2022 |
| WO | WO 2022/136916 | 6/2022 |
| WO | WO 2022/221143 | 10/2022 |
| WO | WO 2022/251224 | 12/2022 |
| WO | WO 2022/271731 | 12/2022 |
| WO | WO 2023/064282 | 4/2023 |
| WO | WO 2023/076485 | 5/2023 |
| WO | WO 2023/114871 | 6/2023 |
| WO | WO 2023/114875 | 6/2023 |
| WO | WO 2023/114877 | 6/2023 |
| WO | WO 2024/031048 | 2/2024 |
| WO | WO 2024/059696 | 3/2024 |

(Continued)

OTHER PUBLICATIONS

Chen, et al., "Asymmetric Reduction of Prochiral Ketones Using Chirally Modified Sodium Borohydride" *J China Pharm. U.* (2000) 31(5):327-329.

(Continued)

*Primary Examiner* — Joseph K McKane
*Assistant Examiner* — Jalisa Holmes Ferguson
(74) *Attorney, Agent, or Firm* — Knobbe, Martens, Olson & Bear, LLP

(57) ABSTRACT

Disclosed herein are methods for preparing tertiary alcohols from an optionally substituted phenyl ketone or an optionally substituted pyridinyl ketone that includes the use of a chiral ligand and boron trifluoride diethyl etherate. Tertiary alcohols can be used to prepare synthetic versions of natural products and/or pharmaceuticals.

19 Claims, 1 Drawing Sheet

(56) References Cited

FOREIGN PATENT DOCUMENTS

Figure 1:
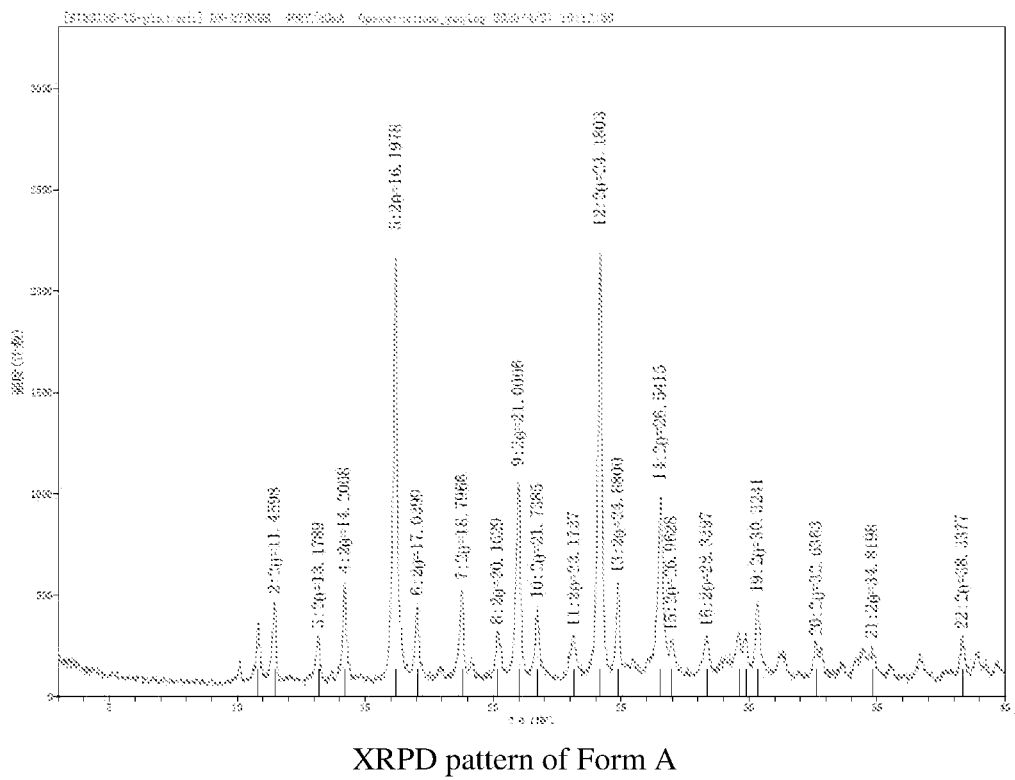

| WO | WO 2024/059808 | 3/2024 |
|----|----------------|--------|
| WO | WO 2024/102649 | 5/2024 |
| WO | WO 2024/102650 | 5/2024 |
| WO | WO 2024/249756 | 12/2024 |
| WO | WO 2025/076311 | 4/2025 |

OTHER PUBLICATIONS

Office Action dated Feb. 22, 2024 for CN Application No. 202080086586.1, filed Nov. 12, 2020.

Bieszczad et al., "Asymmetric Grignard Synthesis of Tertiary Alcohols through Rational Ligand Design" Angew. Chem. Int. Ed. (2017) 56:4272-4276.

Friel et al., "Aluminum-Catalyzed Asymmetric Alkylations of Pyridyl-Substituted Alkynyl Ketones with Dialkylzinc Reagents" J. Am. Chem. Soc. (2008) 130:9942-9951.

Hatano et al., "Recent Progress in the Catalytic Synthesis of Tertiary Alcohols from Ketones with Organometallic Reagents" Synthesis (2008) 11:1647-1675.

Hatano et al., "Catalytic enantioselective synthesis of sterically demanding alcohols using di(2°-alkyl) zinc prepared by the refined Charette's method" Chem. Commun. (2010) 46:5443-5445.

Hatano et al., "Catalytic enantioselective alkyl and aryl addition to aldehydes and ketones with organozinc reagents derived from alkyl Grignard reagents or arylboronic acids" Catal. Sci. Technol. (2011) 1:1149-1158.

Jeon et al., "A Green Chemistry Approach to a More Efficient Asymmetric Catalyst: Solvent-Free and Highly Concentrated Alkyl Additions to Ketones" J. Am. Chem. Soc. (2005) 127:16416-16425.

Jeon et al., "Catalytic Asymmetric Addition of Alkylzinc and Functionalized Alkylzinc Reagents to Ketones" J. Org. Chem. (2005) 70:448-455.

Özdemirhan, et al., "Enzyme-catalyzed resolution of aromatic ring fused cyclic tertiary alcohols" Asymmetry (2008) 19:2717-2720.

Ramon, et al., "Chiral Tertiary Alcohols Made by Catalytic Enantioselective Addition of Unreactive Zinc Reagents to Poorly Electrophilic Ketones?" Angew. Chem. Int. Ed. (2004) 43:284-287.

Riant, et al., "Asymmetric catalysis for the construction of quaternary carbon centres: nucleophilic addition on ketones and ketimines" Org. Biomol. Chem. (2007) 5:873-888.

Stymiest, et al., "Enantiodivergent conversion of chiral secondary alcohols into tertiary alcohols" Nature Letters (2008) 456:778-782.

Walsh, Patrick J., "Titanium-Catalyzed Enantioselective Additions of Alkyl Groups to Aldehydes: Mechanistic Studies and New Concepts in Asymmetric Catalysis" Acc. Chem. Res. (2003) 36:739-749.

Yus et al., "Synthesis of new C2-symmetrical bis(hydroxycamphorsulfonamide) ligands and their application in the enantioselective addition of dialkylzinc reagents to aldehydes and ketones" Tetrahedron: Asymmetry (2003) 14:1103-1114.

Hatano et al., "Highly active chiral phosphoramide-Zn(II) complexes as conjugate acid-base catalysts for enantioselective organozinc addition to ketones" Organic letters (2007) 9(22):4535-4538.

Hatano et al. "Commercially available neat organozincs as highly reactive reagents for catalytic enantioselective addition to ketones and aldehydes under solvent free conditions" Tetrahedron (2011) 67(24):4417-4424.

International Search Report and Written Opinion mailed Jan. 22, 2021 for PCT Application No. PCT/US2020/060298 filed Nov. 12, 2020.

International Preliminary Report on Patentability issued May 17, 2022 for PCT Application No. PCT/US2020/060298, filed Nov. 12, 2020.

Office Action dated Feb. 20, 2025 for Israeli Patent Application No. 292920, filed Nov. 12, 2020.

Office Action dated Feb. 14, 2025 for Russian Patent Application No. 2022112264, filed Nov. 12, 2020.

Deryabina et al., "Practical Course in Organic Chemistry Part II. Reactions of Organic Compounds," Samara State University (2007).

Forrat et al., "Trans-1-Sulfonylamino-2-isoborneolsulfonyl-aminocyclohexane derivatives: excellentchiral ligands for the catalytic enantioselective addition of organozinc reagents to ketones," Chem. Eur. J. (2006) 12(16):4431-4445.

Huang et al., "Constructing a Quantitative Correlation between N-Substituent Sizes of Chiral Ligands and Enantioselectivities in Asymmetric Addition Reactions of Diethylzinc with Benzaldehyde, Journal of Organic Chemistry," J. Org. Chem. (2012) 77(22):10427-10434.

Ojida et al., "Highly Enantioselective Reformatsky Reaction of Ketones: Chelation-Assisted Enantioface Discrimination," Org. Lett. (2002) 4(18): 3051-3054.

Xie et al., " ChemInform Abstract: Design and Synthesis of New Chiral Pyridine-Phosphite Ligands for the Copper-Catalyzed Enantioselective Conjugate Addition of Diethylzinc to Acyclic Enones," Asymmetry (2009) 20:1425-1432.

Office Action and Search Report dated Jul. 23, 2024 for Taiwan Patent Application No. 109139816, filed Nov. 13, 2020.

Office Action dated Apr. 27, 2024 for Russian Patent Application No. 2022112264, filed Nov. 12, 2020.

Office Action dated Nov. 12, 2024 for JP Application No. 2022-528146, filed Nov. 12, 2020.

Office Action dated Sep. 23, 2024 for Russian Patent Application No. 2022112264, filed Nov. 12, 2020.

Second Office Action dated Jul. 3, 2024 for Chinese Patent Application No. 202080086586.1, filed Nov. 12, 2020.

Extended European Search Report dated Oct. 26, 2023 for EP Application No. 20887780, filed Nov. 12, 2020.

"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.

* cited by examiner

XRPD pattern of Form A

XRPD pattern of Form B

CHIRAL SYNTHESIS OF A TERTIARY ALCOHOL

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 62/935,894, filed Nov. 15, 2019, and 62/037,761, filed Jun. 11, 2020.

BACKGROUND

Field

The present application relates to the fields of chemistry and medicine. More particularly, disclosed herein are methods of preparing tertiary alcohols. Also disclosed herein are methods of using the tertiary alcohols in the preparation of compounds that may be used as anti-cancer agents.

Description

New methods for preparing chiral compounds with high enantiomeric purity while minimizing undesirable side products are highly valuable. Chiral secondary and tertiary alcohols are often used in the preparation of synthetic versions of natural products and pharmaceuticals. There are many methods to prepare chiral secondary alcohols. However, methods that provide chiral tertiary alcohols with high enantiomeric purity and high yield continues to be a challenge.

SUMMARY

Some embodiments disclosed herein relate to a method of preparing a tertiary alcohol, or a salt thereof, that can include combining: an optionally substituted phenyl ketone or an optionally substituted pyridinyl ketone, or a salt of any of the foregoing, wherein when the phenyl ketone or pyridinyl ketone is substituted, the phenyl ketone and pyridinyl ketone is substituted with one or more substituents selected from the group consisting of halogen, an unsubstituted $C_{1-4}$ alkyl and an unsubstituted $C_{1-4}$ alkoxy; a zinc reagent selected from $Et_2Zn$, $Me_2Zn$ and $Ph_2Zn$; a chiral ligand having the structure

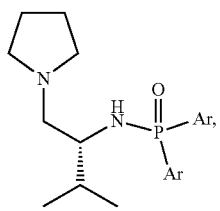

wherein each Ar can be independently an unsubstituted or a substituted phenyl or an unsubstituted or a substituted naphthyl, wherein when an Ar is a substituted phenyl or a substituted naphthyl, the phenyl or the naphthyl can be substituted with one or more substituents independently selected from halogen, an unsubstituted $C_{1-4}$ alkyl and an unsubstituted $C_{1-4}$ alkoxy; and $BF_3 \cdot OEt_2$.

Some embodiments disclosed herein relate to a compound of the following Formula (G1-a), or a salt thereof, having the structure:

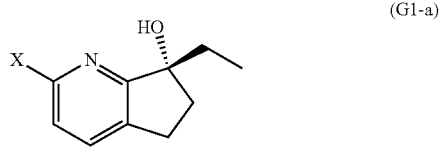

wherein X is Cl, Br or I. In some embodiments, X is Cl. In some embodiments, X is Br. In some embodiments, X is I.

DRAWINGS

FIG. 1 provides representative X-ray powder diffraction (XRPD) patterns of Form A of (R)-2-Chloro-7-ethyl-6,7-dihydro-5H-cyclopenta[b]pyridin-7-ol.

Figure 2:
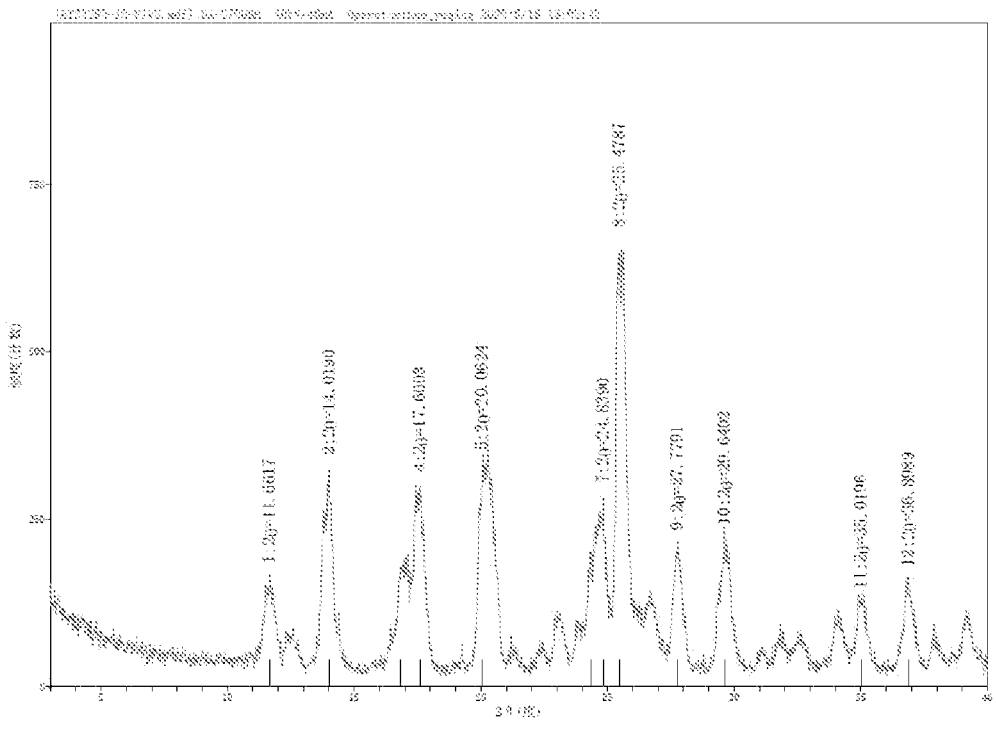

FIG. 2 provides representative X-ray powder diffraction (XRPD) patterns of Form B of (R)-2-Chloro-7-ethyl-6,7-dihydro-5H-cyclopenta[b]pyridin-7-ol.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" and "X" group(s) such as, without limitation, $R^{1a}$, $R^{1b}$, $R^{2a}$, $R^{2b}$, $R^{3a}$, $R^{3b}$, $R^{4b}$, $R^{5b}$, $R^{1g}$, $R^{2g}$, $R^{3g}$, $R^{1h}$, $R^{2h}$, $R^{3h}$, $R^{1j}$, $R^{2j}$, $R^{3j}$, $R^{1k}$, $R^{2k}$, $R^{3k}$, $R^{4k}$, $R^{5k}$, $R^{1l}$, $R^{2l}$, $R^{3l}$, $R^{4l}$, $R^{5l}$, $R^{1m}$, $R^{2m}$, $R^{3m}$, $R^{4m}$, $R^{5m}$, $X^{1a}$, $X^{2a}$, $X^{3a}$, $X^{4a}$, $X^{1g}$, $X^{1h}$, $X^{1j}$, $X^{2g}$, $X^{3g}$, $X^{4g}$, $X^{2h}$, $X^{3h}$, $X^{4h}$, $X^{2j}$, $X^{3j}$ and $X^{4j}$ represent substituents that can be attached to the indicated atom(s). Such R and/or X groups may be referred to herein in a general way as "R" or "X" groups. If two "R" groups are described as being "taken together" the R groups and the atoms they are attached to can form a cycloalkyl, cycloalkenyl, aryl, heteroaryl or heterocycle. For example, without limitation, if Ra and $R^b$ of an $NR^aR^b$ group are indicated to be "taken together," it means that they are covalently bonded to one another to form a ring:

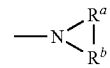

In addition, if two "R" groups are described as being "taken together" with the atom(s) to which they are attached to form a ring as an alternative, the R groups are not limited to the variables or substituents defined previously.

As used herein, "Ca to Cb" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl, cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. As used herein, the term "fused" refers to two rings which have two atoms and one bond in common. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Typical mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one, two, three or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, those described herein and the following: furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion, as described herein with respect to "cycloalkyl." Additionally, any nitrogens in a heterocyclyl may be quaternized. Heterocyclyl or heteroalicyclic groups may be unsubstituted or substituted. Examples of such "heterocyclyl" groups include, but are not limited to, those described herein and the following: 1,3-dioxin, 1,3-dioxane, 1,4-dioxane, 1,2-dioxolane, 1,3-dioxolane, 1,4-dioxolane, 1,3-oxathiane, 1,4-oxathiin, 1,3,4-oxadiazol-2(3H)-one, 1,2,3-oxadiazol-5(2H)-one, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "cycloalkyl(alkyl)" refers to a cycloalkyl group connected, as a substituent, via a lower alkylene group. The lower alkylene and cycloalkyl group of an cycloalkyl(alkyl) may be substituted or unsubstituted. Examples include but are not limited to cyclohexyl(methyl), cyclopentyl(methyl), cyclohexyl(ethyl) and cyclopentyl (ethyl).

As used herein, "aryl(alkyl)" refers to an aryl group connected, as a substituent, via a lower alkylene group. The lower alkylene and aryl group of an aryl(alkyl) may be substituted or unsubstituted. Examples include but are not limited to benzyl, 2-phenylalkyl, 3-phenylalkyl and naphthylalkyl.

As used herein, "heteroaryl(alkyl)" refers to a heteroaryl group connected, as a substituent, via a lower alkylene group. The lower alkylene and heteroaryl group of a heteroaryl(alkyl) may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "heterocyclyl(alkyl)" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl), and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) as defined herein. A non-limiting list of alkoxys are methoxy, ethoxy, n-propoxy, 1-methylethoxy (isopropoxy), cyclopropoxy, n-butoxy, iso-butoxy, sec-butoxy, tert-butoxy, cyclobutoxy, phenoxy and benzoxy. An alkoxy may be substituted or unsubstituted.

As used herein, "acyl" refers to an alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include acetyl, propanoyl, benzoyl and acryl. An acyl may be substituted or unsubstituted.

The term "halogen atom" or "halogen" as used herein, means any one of the radio-stable atoms of column 7 of the Periodic Table of the Elements, such as, fluorine, chlorine, bromine and iodine.

A "phenyl ketone" refers to a monocyclic phenyl ketone and a bicyclic phenyl ketone. A monocyclic phenyl group has a "—C(=O)R$^{a1}$" moiety attached to the phenyl ring, wherein R$^{a1}$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A bicyclic phenyl ketone has a phenyl fused to a 4 to 8 membered monocyclic hydrocarbon ring that has a carbonyl moiety attached to one of the ring carbons of the hydrocarbon ring, wherein 1 or 2 ring carbons of the hydrocarbon ring can be replaced with a heteroatom independently selected from oxygen (O) and sulfur (S).

A "pyridinyl ketone" refers to a monocyclic pyridinyl ketone and a bicyclic pyridinyl ketone. A monocyclic pyridinyl group has a "—C(=O)R$^{b1}$" moiety attached to the phenyl ring, wherein R$^{b1}$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A bicyclic pyridinyl ketone has a pyridinyl fused to a 4 to 8 membered monocyclic hydrocarbon ring that has a carbonyl moiety attached to one of the ring carbons of the hydrocarbon ring, wherein 1 or 2 ring carbons of the hydrocarbon ring can be replaced with a heteroatom independently selected from oxygen (O) and sulfur (S).

Where the numbers of substituents is not specified (e.g. alkoxyphenyl), there may be one or more substituents present. For example "alkoxyphenyl" may include one or more of the same or different alkoxy groups. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Unless otherwise specified, the term "crystalline" and related terms used herein, when used to describe a substance, component, product or form, mean that the substance, component, product or form is substantially crystalline, for example, as determined by X-ray diffraction. (see, e.g., *Remington's Pharmaceutical Sciences*, 20$^{th}$ ed., Lippincott Williams & Wilkins, Philadelphia Pa., 173 (2000); *The United States Pharmacopeia*, 37$^{th}$ ed., 503-509 (2014)).

As used herein, and unless otherwise specified, the terms "about" and "approximately," when used in connection with a numeric value or range of values which is provided to characterize a particular solid form, e.g., a specific temperature or temperature range (for example, that describes a melting, dehydration, desolvation or glass transition temperature); a mass change (for example, a mass change as a function of temperature or humidity); a solvent or water content (for example, mass or a percentage); or a peak position (for example, in analysis by, for example, IR or Raman spectroscopy or XRPD); indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies and dissolution studies. In some embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. In the context of molar ratios, "about" and "approximately" indicate that the numeric value or range of values may vary within 20%, 15%, 10%, 9%, 8%, 7%, 6%, 5%, 4%, 3%, 2%, 1.5%, 1%, 0.5%, or 0.25% of the recited value or range of values. It should be understood that the numerical values of the peaks of an X-ray powder diffraction pattern may vary from one machine to another, or from one sample to another, and so the values quoted are not to be construed as absolute, but with an allowable variability, such as ±0.2 degrees two theta (° 2θ), or more. For example, in some embodiments, the value of an XRPD peak position may vary by up to ±0.2 degrees 2θ while still describing the particular XRPD peak.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z, or a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds and Methods of Preparation

Some embodiment described herein relate to a method of preparing a tertiary alcohol, or a salt thereof, that can include combining: an optionally substituted phenyl ketone or an optionally substituted pyridinyl ketone, or a salt of any of the foregoing; a zinc reagent selected from $Et_2Zn$, $Me_2Zn$ and $Ph_2Zn$; a chiral ligand having the structure

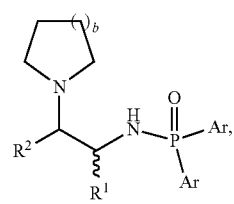

wherein $R^1$ can be $-CH_3$, $-CH_2CH_3$, $-CH(CH_3)_2$ or $-C(CH_3)_3$; $R^2$ can be H; or $R^1$ and $R^2$ can be taken together along with the carbons to which each $R^1$ and $R^2$ are attached to form an unsubstituted cyclohexyl ring; each Ar can be independently an unsubstituted or a substituted phenyl or an unsubstituted or a substituted naphthyl, wherein when an Ar is a substituted phenyl or a substituted naphthyl, the phenyl or the naphthyl can be substituted with one or more substituents independently selected from halogen, an unsubstituted $C_{1-4}$ alkyl and an unsubstituted $C_{1-4}$ alkoxy; and b can be 1 or 2; and $BF_3.OEt_2$.

Some embodiment described herein relate to a method of preparing a tertiary alcohol, or a salt thereof, that can include combining: an optionally substituted phenyl ketone or an optionally substituted pyridinyl ketone, or a salt of any of the foregoing; a zinc reagent selected from $Et_2Zn$, $Me_2Zn$ and $Ph_2Zn$; a chiral ligand having the structure

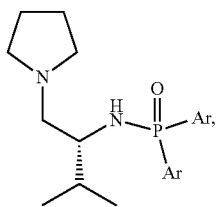

wherein each Ar can be independently an unsubstituted or a substituted phenyl or an unsubstituted or a substituted naphthyl, wherein when an Ar is a substituted phenyl or a substituted naphthyl, the phenyl or the naphthyl can be substituted with one or more substituents independently selected from halogen, an unsubstituted $C_{1-4}$ alkyl and an unsubstituted $C_{1-4}$ alkoxy; and $BF_3.OEt_2$.

The optionally substituted phenyl ketone can have a variety of structures. For example, the optionally substituted phenyl ketone can be bicyclic and have a carbonyl attached to a ring carbon of a 4 to 8 membered monocyclic hydrocarbon ring, wherein the hydrocarbon ring is fused to the phenyl group, and wherein 1 to 2 of the carbons of the hydrocarbon ring can be replaced with a heteroatom independently selected from O (oxygen) and S (sulfur). As another example, the optionally substituted phenyl ketone can be monocyclic, wherein an acyl can be attached to the phenyl group.

In some embodiments, the optionally substituted phenyl ketone can have a structure selected from a compound of Formula (A) and a compound of Formula (B):

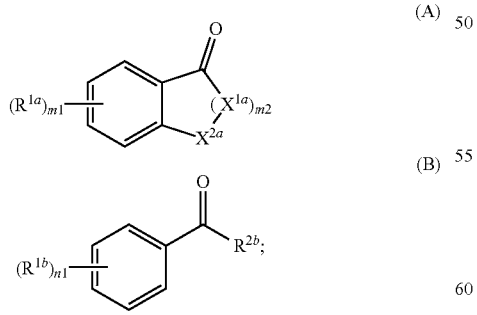

wherein: m1 can be 0, 1, 2, 3 or 4; n1 can be 0, 1, 2, 3, 4 or 5; m2 can be 1 or 2; $X^{1a}$ can be —$CH_2$—; $X^{2a}$ can be —$CH_2$—, —$CH(CH_3)$—, —$C(CH_3)_2$— or O (oxygen); each $R^{1a}$ and each $R^{1b}$ can be independently selected from halogen, an unsubstituted $C_{1-4}$ alkyl and an unsubstituted $C_{1-4}$ alkoxy; and $R^{2b}$ can be an unsubstituted $C_{1-4}$ alkyl. Non-limiting examples of optionally substituted ketones include the following:

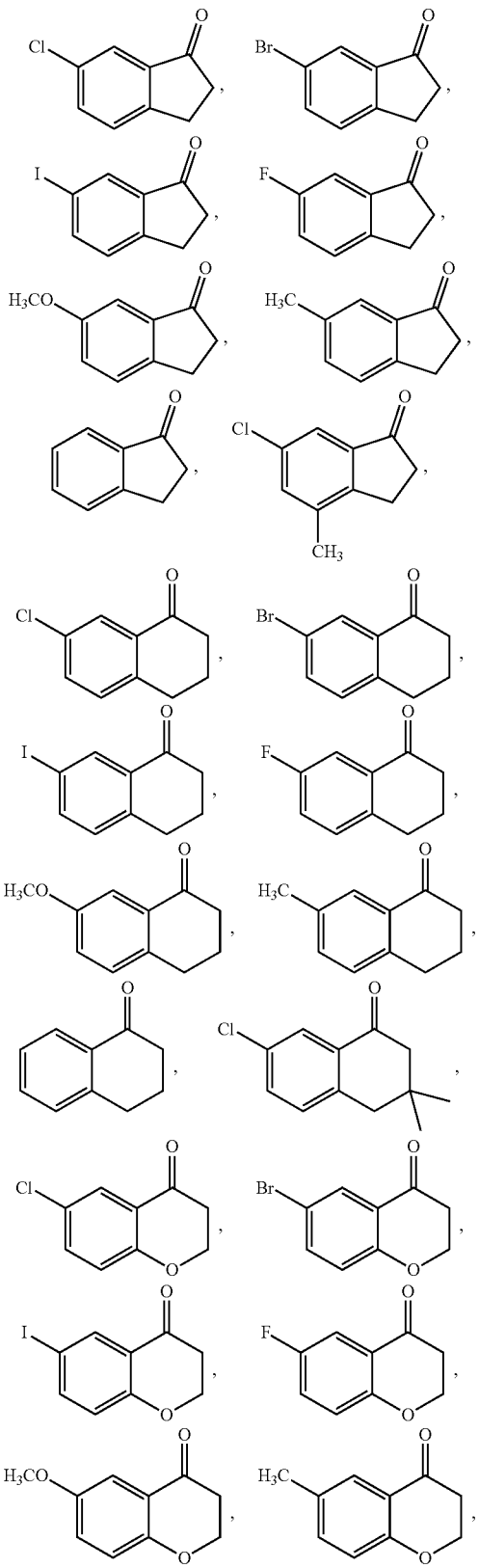

-continued

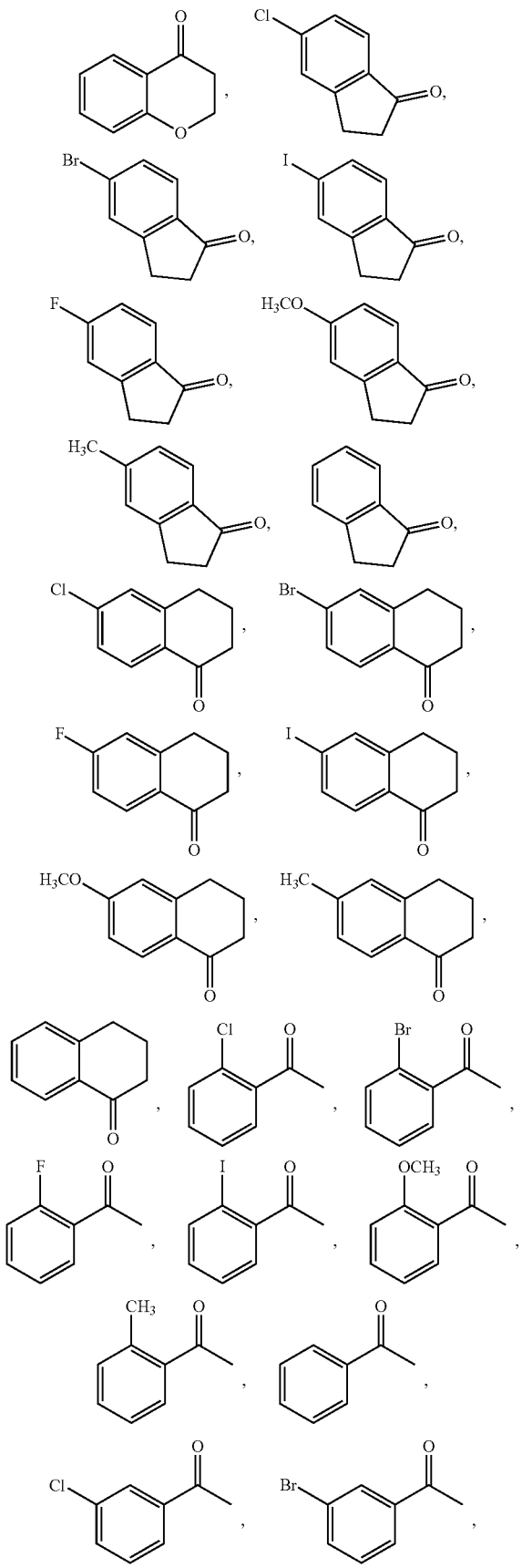

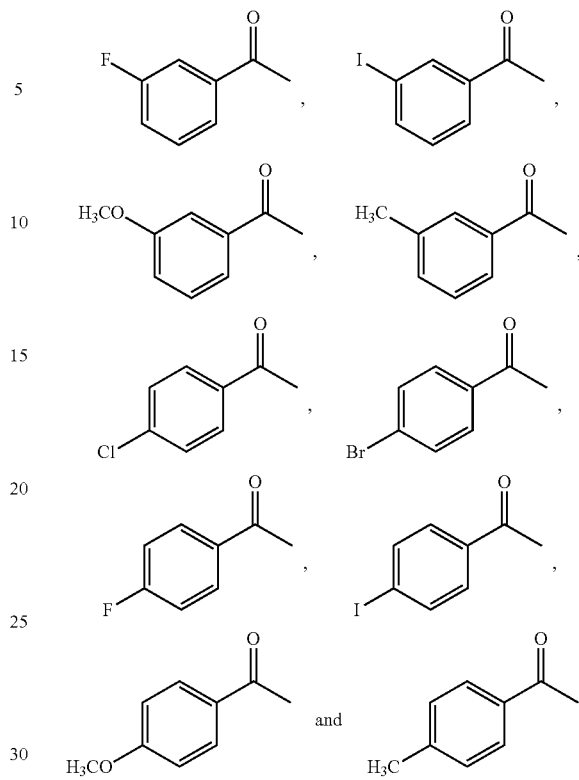

Various optionally substituted pyridinyl ketones can be also used in methods described herein. As described herein, the optionally substituted pyridinyl ketone can be monocyclic or bicyclic. When the optionally substituted pyridinyl ketone is bicyclic, a carbonyl can be attached to a ring carbon of a 4 to 8 membered monocyclic hydrocarbon ring, wherein the hydrocarbon ring may have 1 to 2 ring carbons replaced with a heteroatom independently selected from O (oxygen) and S (sulfur), and wherein the hydrocarbon ring is fused to the pyridinyl group. When the optionally substituted pyridinyl ketone is monocyclic, an acyl can be appended to the pyridinyl group.

In some embodiments, the optionally substituted pyridinyl ketone can have a structure selected from a compound of Formula (G), a compound of Formula (H), a compound of Formula (J), a compound of Formula (K), a compound of Formula (L) and a compound of Formula (M):

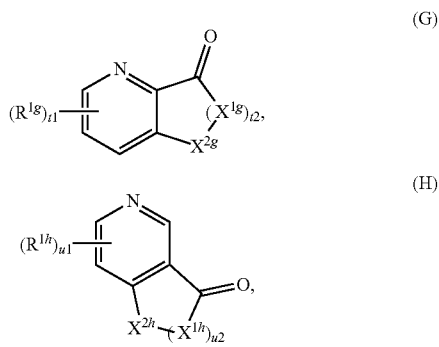

-continued

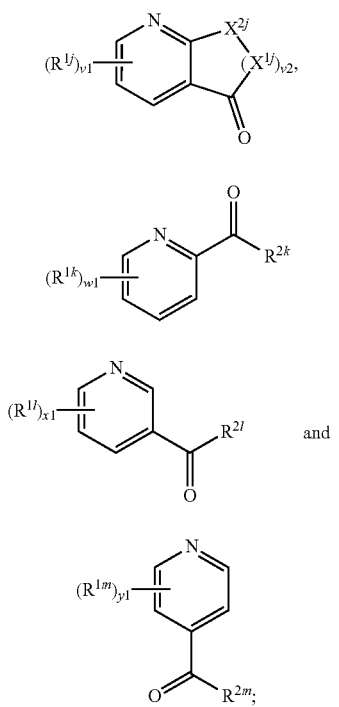

wherein: t1, u1 and v1 can be independently 0, 1, 2 or 3; w1, x1 and y1 can be independently 0, 1, 2, 3 or 4; t2, u2 and v2 can be independently 1 or 2; $X^{1g}$, $X^{1h}$ and $X^{1i}$ can be each —$CH_2$—; $X^{2g}$, $X^{2h}$ and $X^{2j}$ can be independently —$CH_2$—, —$CH(CH_3)$—, —$C(CH_3)_2$— or O; $R^{1g}$, $R^{1h}$, $R^{1j}$, $R^{1k}$, $R^{1l}$ and $R^{1m}$ can be independently selected from halogen, an unsubstituted $C_{1-4}$ alkyl and an unsubstituted $C_{1-4}$ alkoxy; and $R^{2k}$, $R^{2l}$ and $R^{2m}$ can be independently an unsubstituted $C_{1-4}$ alkyl. A non-limiting list of optionally substituted pyridinyl ketones include the following:

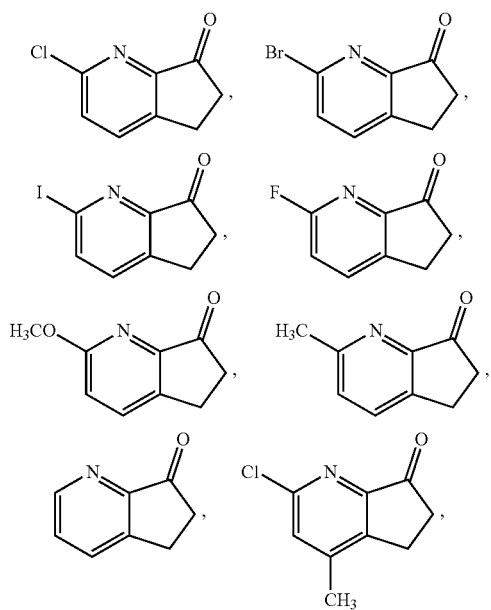

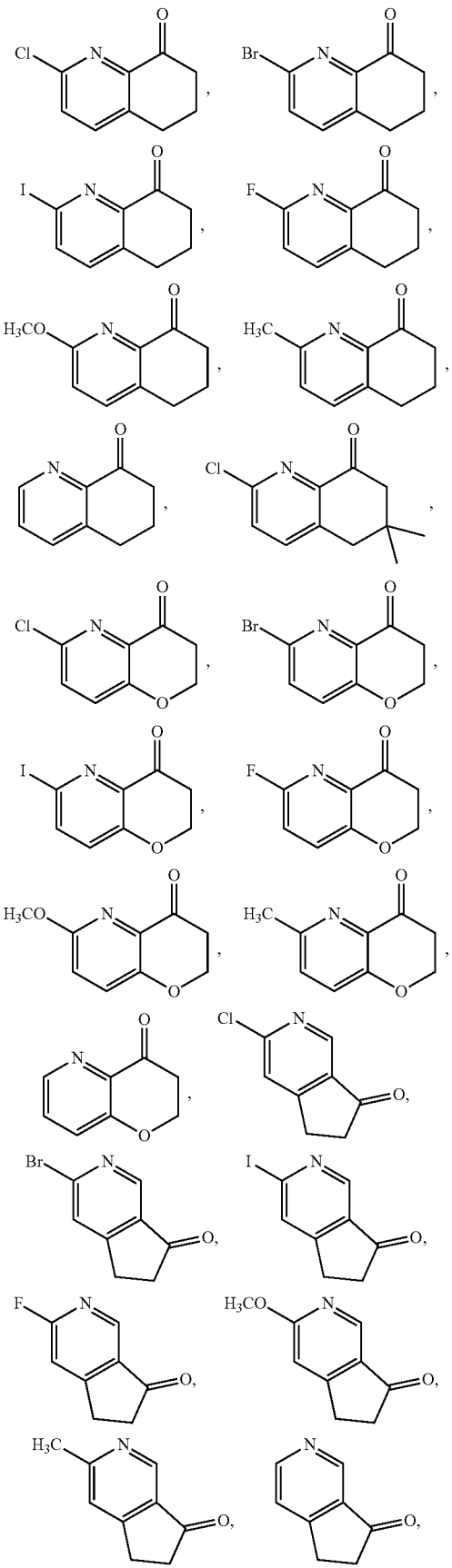

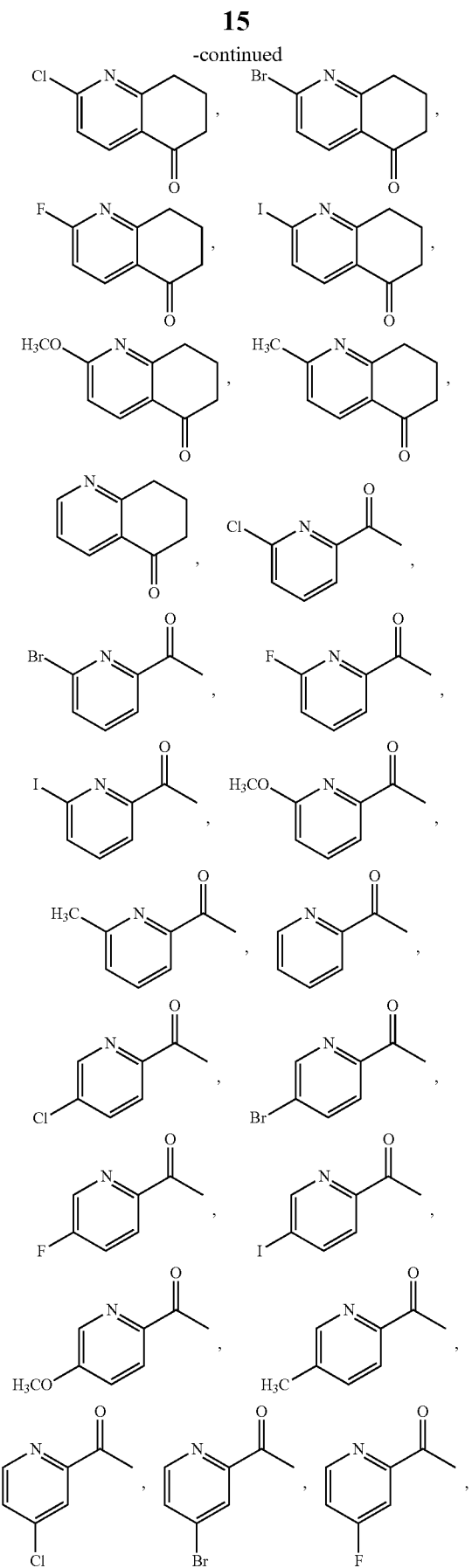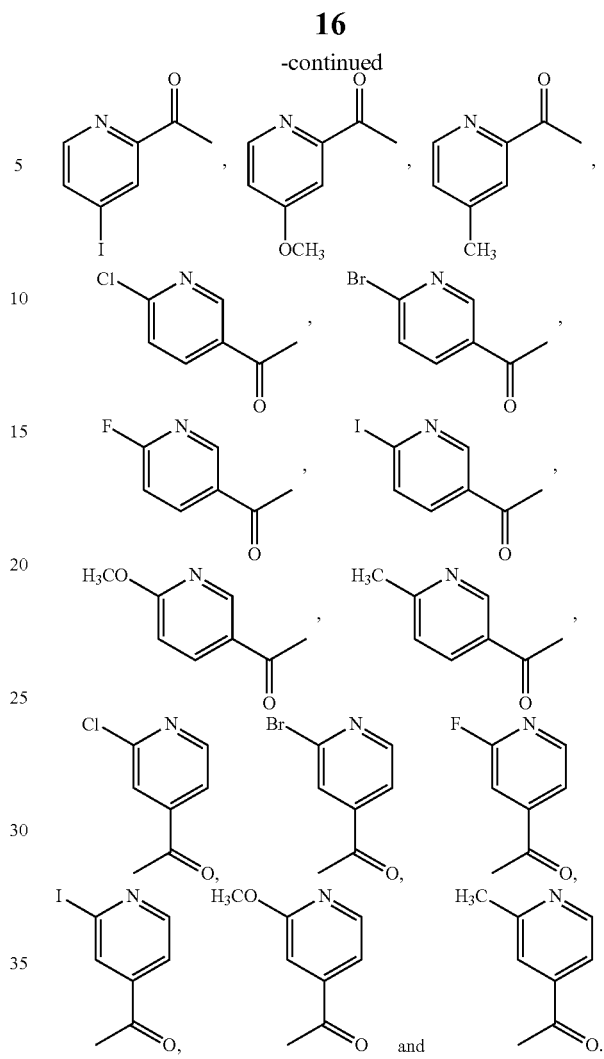

As described herein, an optionally substituted phenyl ketone and/or an optionally substituted pyridinyl can be used to provide a tertiary alcohol. For example, an optionally substituted phenyl ketone and/or an optionally substituted pyridinyl ketone can be used in a method described herein to provide a chiral tertiary alcohol in high yield and/or high enantiomeric purity. Examples of tertiary alcohols that can be obtained by a method described herein include, but are not limited to, a compound of Formula (A1) and a compound of Formula (B1):

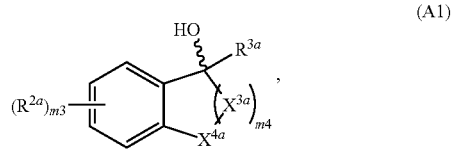

(A1)

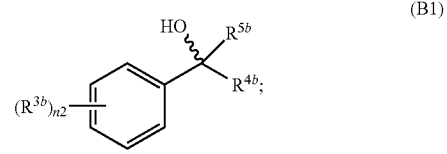

(B1)

wherein: m3 can be 0, 1, 2, 3 or 4; n2 can be 0, 1, 2, 3, 4 or 5; m4 can be 1 or 2; $X^{3a}$ can be —CH$_2$—; $X^{4a}$ can be —CH$_2$—, —CH(CH$_3$)—, —C(CH$_3$)$_2$— or O (oxygen); each R$^{2a}$ and each R$^{3b}$ can be independently selected from halogen, an unsubstituted C$_{1-4}$ alkyl and an unsubstituted C$_{1-4}$ alkoxy; R$^{4b}$ can be an unsubstituted C$_{1-4}$ alkyl; and R$^{3a}$ and R$^{5b}$ can be independently —CH$_3$, —CH$_2$CH$_3$ or -Ph. Additional examples of tertiary alcohols that can be obtained by a method described herein include, but are not limited to, having a structure selected from a compound of Formula (G1), a compound of Formula (H1), a compound of Formula (J1), a compound of Formula (K1), a compound of Formula (L1) and a compound of Formula (M1):

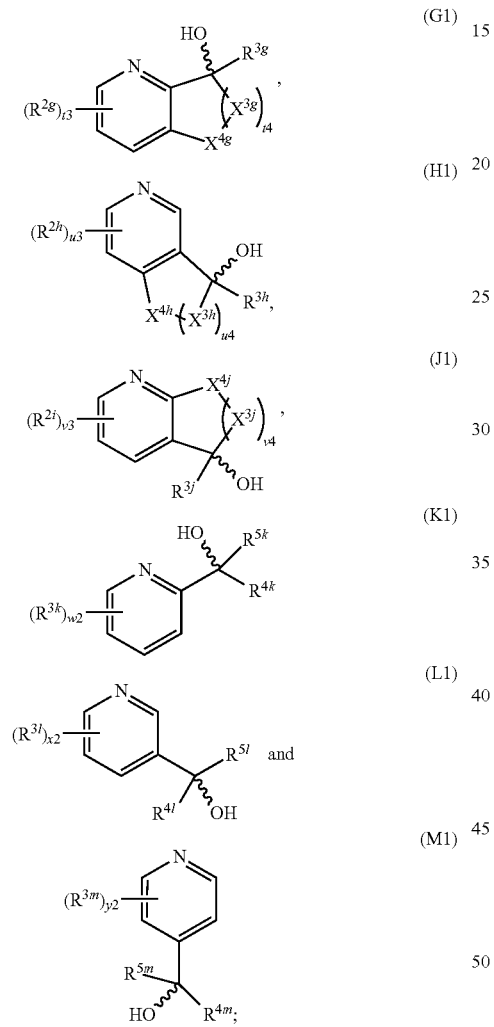

wherein: t3, u3 and v3 can be independently 0, 1, 2 or 3; w2, x2 and y2 can be independently 0, 1, 2, 3 or 4; t4, u4 and v4 can be independently 1 or 2; X$^{3g}$, X$^{3h}$ and X$^{3j}$ can be each —CH$_2$—; X$^{4g}$, X$^{4h}$ and X$^{4j}$ can be independently —CH$_2$—, —CH(CH$_3$)—, —C(CH$_3$)$_2$— or O (oxygen); R$^{2g}$, R$^{2h}$, R$^{2j}$, R$^{3k}$, R$^{3l}$ and R$^{3m}$ can be independently selected from halogen, an unsubstituted C$_{1-4}$ alkyl and an unsubstituted C$_{1-4}$ alkoxy; R$^{4k}$, R$^{4l}$ and R$^{4m}$ can be independently an unsubstituted C$_{1-4}$ alkyl; and R$^{3g}$, R$^{3h}$, R$^{3j}$, R$^{5k}$, R$^{5l}$ and R$^{5m}$ can be independently —CH$_3$, —CH$_2$CH$_3$ or -Ph.

A variety of structures for a tertiary alcohol that can be obtained by a method described herein include, but are not limited to, the following:

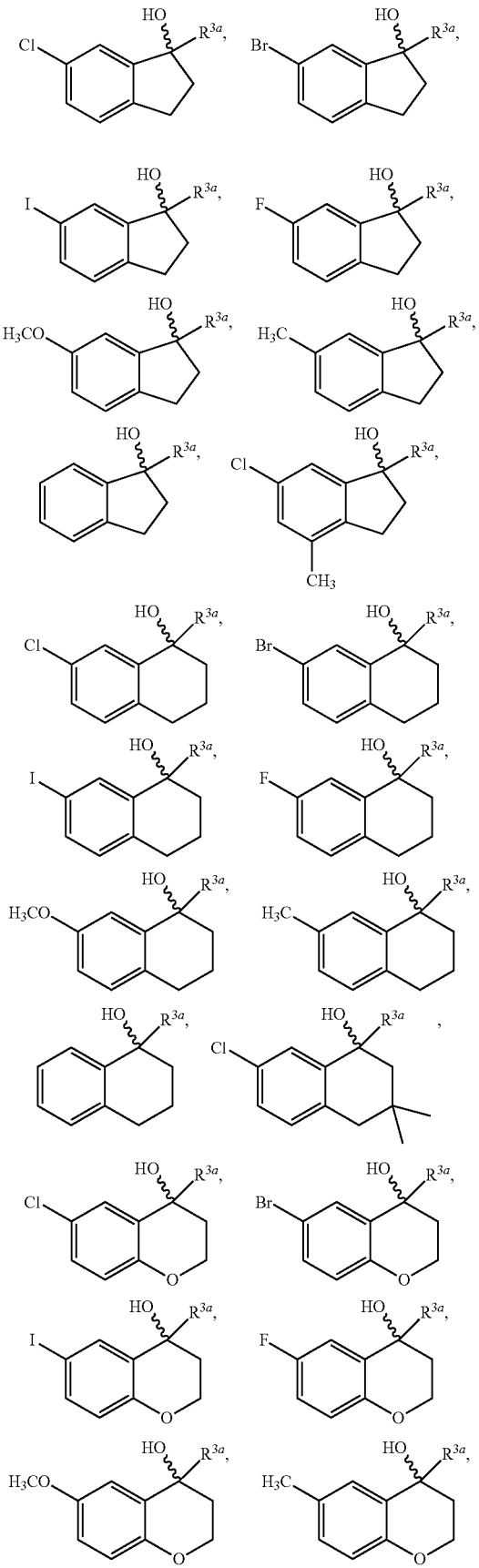

-continued
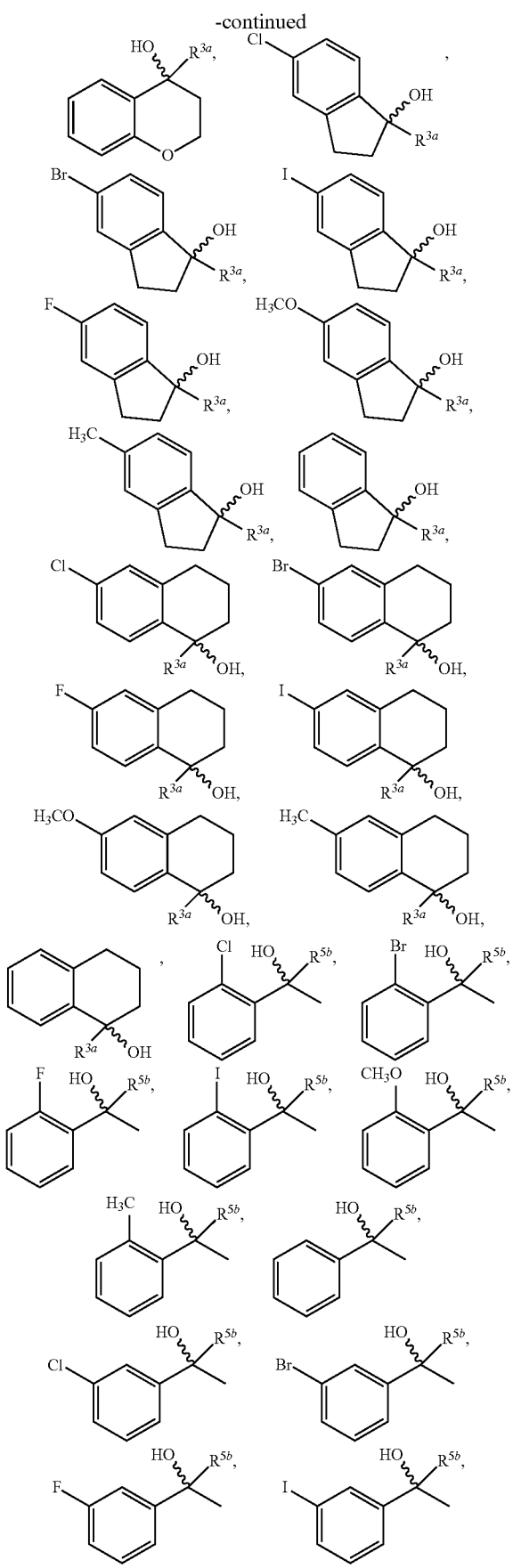
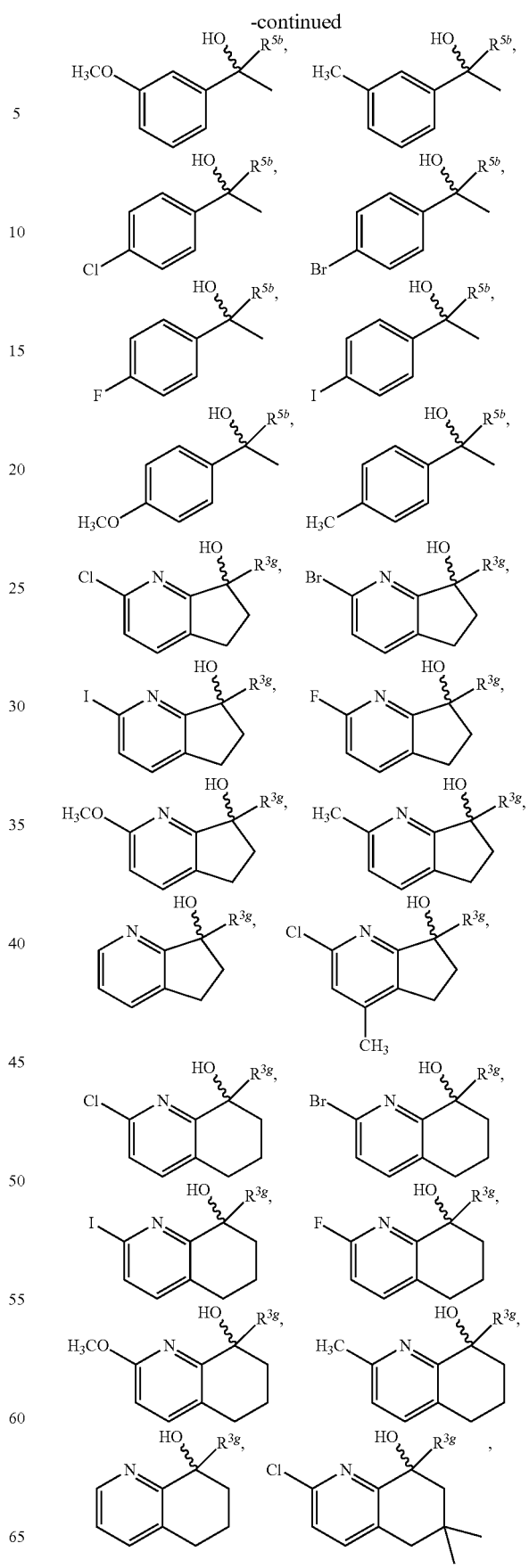

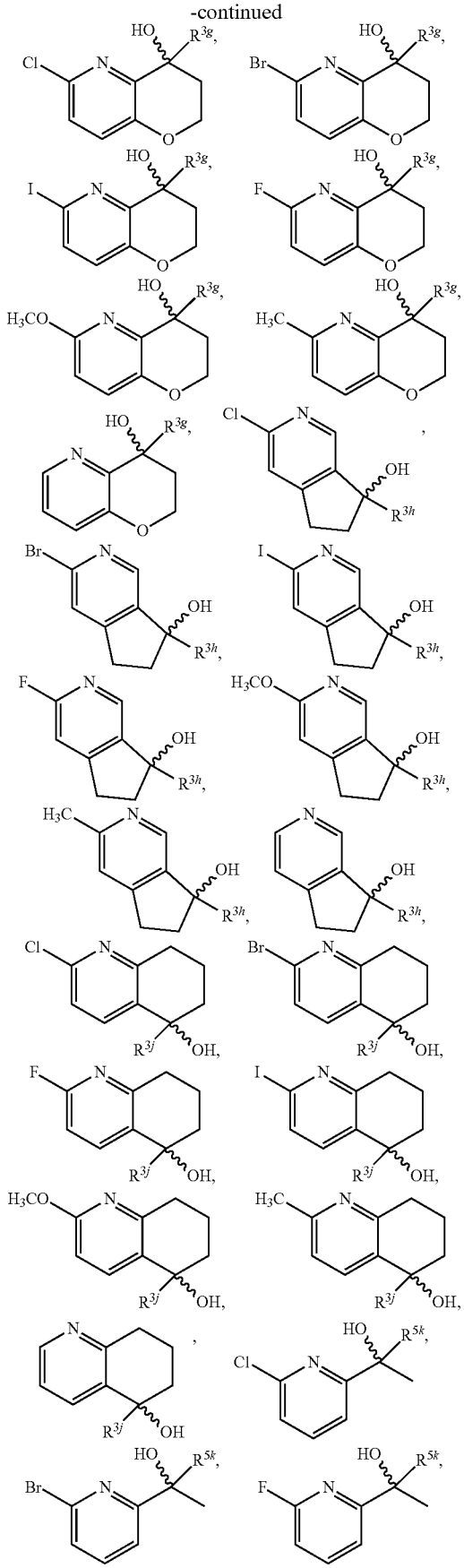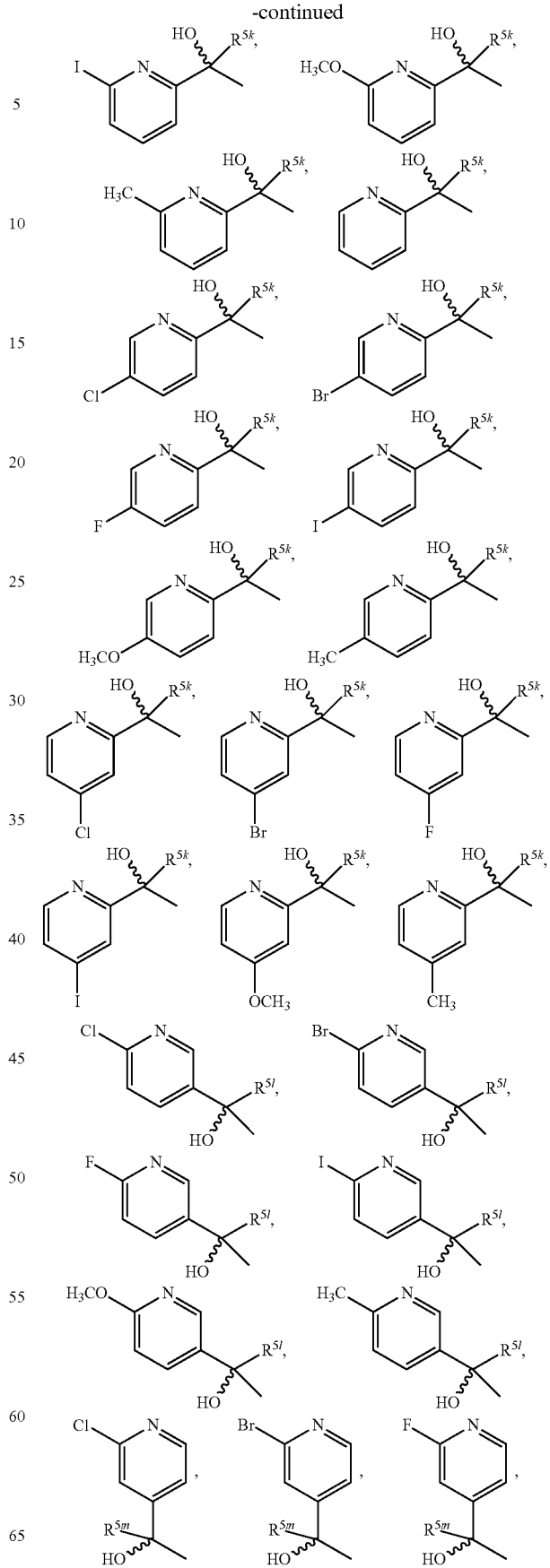

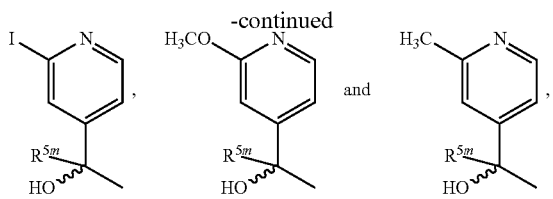

wherein $R^{3a}$, $R^{3g}$, $R^{3h}$, $R^{3j}$, $R^{5b}$, $R^{5k}$, $R^{5l}$ and/or $R^{5m}$ are described herein. In some embodiments, including those of this paragraph, $R^{3a}$, $R^{3g}$, $R^{3h}$, $R^{3j}$, $R^{5b}$, $R^{5k}$, $R^{5l}$ and/or $R^{5m}$ can be an unsubstituted $C_{1-4}$ alkyl. In some embodiments, including those of this paragraph, $R^{3a}$, $R^{3g}$, $R^{3h}$, $R^{3j}$, $R^{5b}$, $R^{5k}$, $R^{5l}$ and/or $R^{5m}$ can be —CH$_2$CH$_3$.

A chiral ligand having the structure

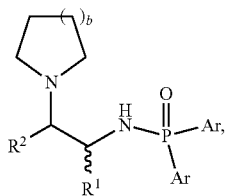

wherein $R^1$ can be —CH$_3$, —CH$_2$CH$_3$, —CH(CH$_3$)$_2$ or —C(CH$_3$)$_3$; $R^2$ can be H; or $R^1$ and $R^2$ can be taken together along with the carbons to which each $R^1$ and $R^2$ are attached to form an unsubstituted cyclohexyl ring; each Ar can be independently an unsubstituted or a substituted phenyl or an unsubstituted or a substituted naphthyl, wherein when an Ar is a substituted phenyl or a substituted naphthyl, the phenyl or the naphthyl can be substituted with one or more substituents independently selected from halogen, an unsubstituted $C_{1-4}$ alkyl and an unsubstituted $C_{1-4}$ alkoxy; and b can be 1 or 2; can be used in a method described herein. In some embodiments, the chiral ligand can be

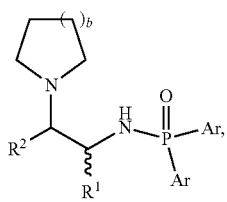

wherein each Ar can be an unsubstituted phenyl. In other embodiments, the chiral ligand has the structure

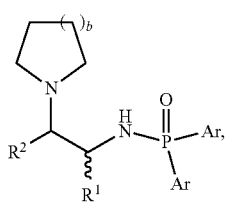

wherein each Ar can be a substituted phenyl substituted with one or more substituents independently selected from the group consisting of halogen, an unsubstituted $C_{1-4}$ alkyl and an unsubstituted $C_{1-4}$ alkoxy. In still other embodiments, the chiral ligand has the structure

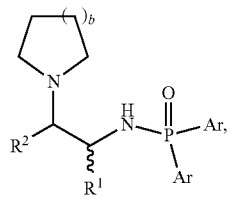

wherein each Ar can be an unsubstituted naphthyl. In yet still other embodiments, the chiral ligand has the structure

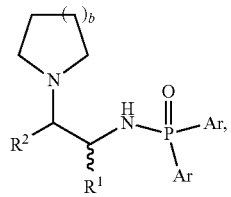

wherein each Ar can be a substituted naphthyl substituted with one or more substituents independently selected from the group consisting of halogen, an unsubstituted $C_{1-4}$ alkyl and an unsubstituted $C_{1-4}$ alkoxy.

The substituent $R^1$ can be a variety of saturated hydrocarbons, such as a $C_{1-4}$ alkyl. The $C_{1-4}$ alkyl can be straight-chained or branched. In some embodiments, $R^1$ can be methyl (—CH$_3$). In other embodiments, $R^1$ can be ethyl (—CH$_2$CH$_3$). In still other embodiments, $R^1$ can be isopropyl (—CH(CH$_3$)$_2$). In yet still other embodiments, $R^1$ can be tert-butyl (—C(CH$_3$)$_3$). Other $C_{1-4}$ alkyls include n-propyl, n-butyl, sec-butyl and iso-butyl. When $R^1$ is a $C_{1-4}$ alkyl, $R^2$ can be hydrogen. A saturated carbocyclic ring can be formed by taking $R^1$ and $R^2$ can be taken together along with the carbons to which each $R^1$ and $R^2$ are attached. In some embodiments, $R^1$ and $R^2$ can be taken together along with the carbons to which each $R^1$ and $R^2$ are attached to form an unsubstituted cyclohexyl ring. Those skilled in the art understand that when $R^1$ is a $C_{1-4}$ alkyl, the carbon to which $R^1$ is attached can be a chiral center. For example, the chiral ligand can have the structure

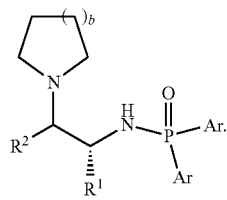

Similarly, when $R^1$ and $R^2$ are taken together along with the carbons to which each $R^1$ and $R^2$ are attached to form an unsubstituted cyclohexyl ring, each of the carbons to which $R^1$ and $R^2$ are attached can be a chiral center. As an example, the chiral ligand can have the structure

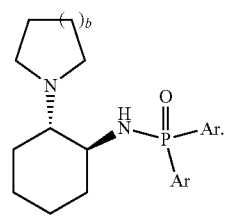

Suitable chiral ligands include, but are not limited to, the following:

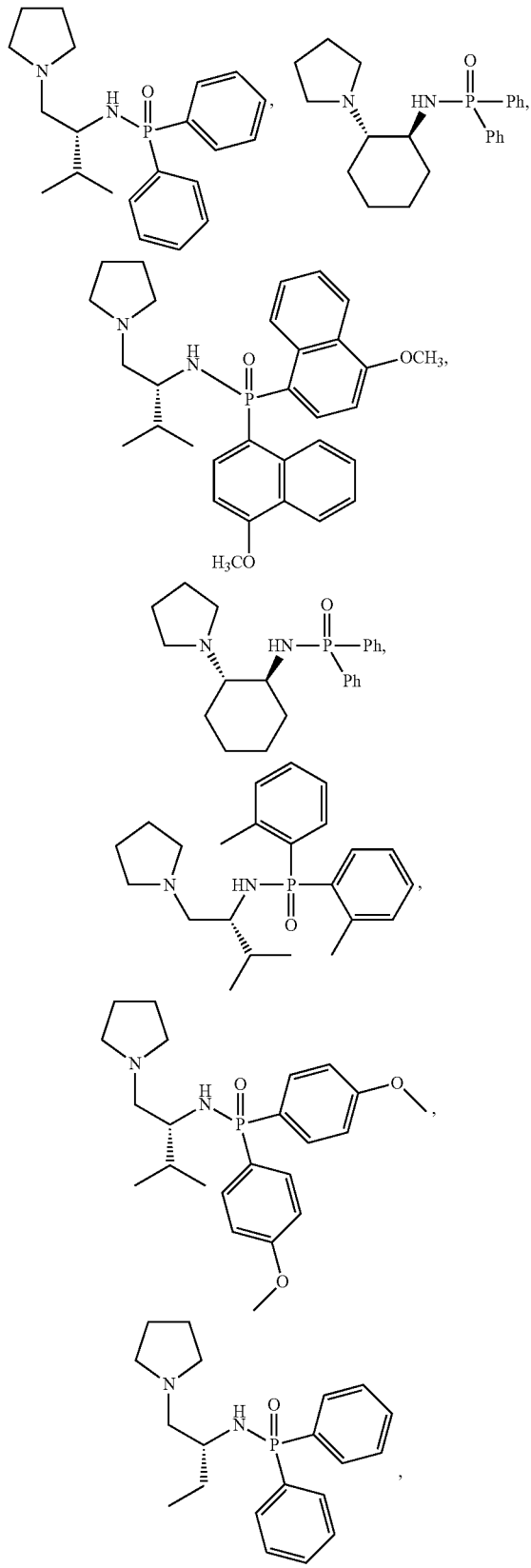

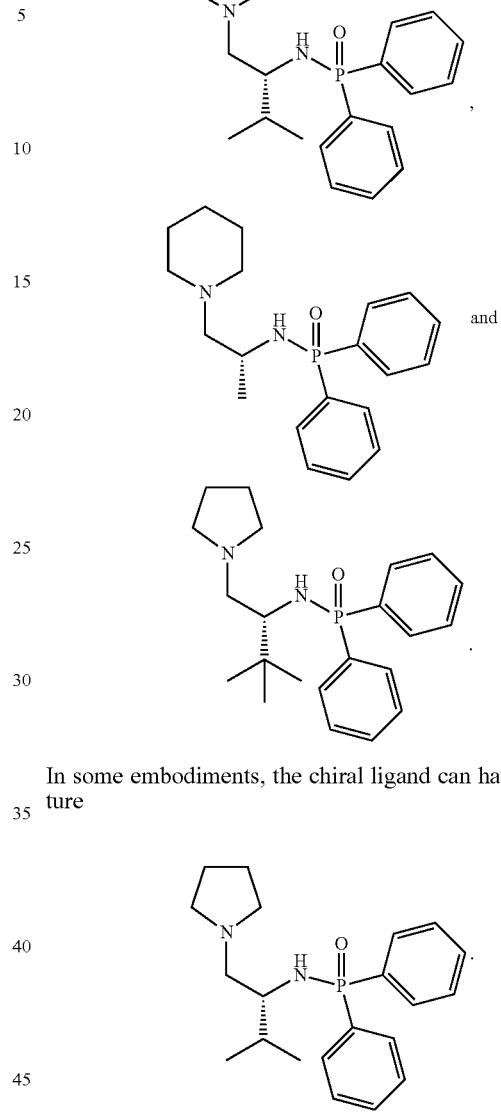

In some embodiments, the chiral ligand can have the structure

Obtaining a tertiary alcohol with high yield and/or high enantiomeric purity can be advantageous for preparing a synthetic version of a natural product and/or pharmaceutical compound. In some embodiments, a tertiary alcohol can be obtained using a method described herein in enantiomeric purity of ≥30%. In some embodiments, a tertiary alcohol can be obtained using a method described herein in enantiomeric purity of ≥40%. In some embodiments, a tertiary alcohol can be obtained using a method described herein in enantiomeric purity of ≥50%. In some embodiments, a tertiary alcohol can be obtained using a method described herein in enantiomeric purity of ≥60%. In some embodiments, a tertiary alcohol can be obtained using a method described herein in enantiomeric purity of ≥70%. In some embodiments, a tertiary alcohol can be obtained using a method described herein in enantiomeric purity of ≥80%. In some embodiments, a tertiary alcohol can be obtained using a method described herein in enantiomeric purity of ≥90%. In some embodiments, a tertiary alcohol can be obtained using a method described herein in enantiomeric purity of ≥95%.

In some embodiments, including those of the previous paragraph, a tertiary alcohol can be obtained using a method described herein in with a yield of ≥50%. In some embodiments, including those of the previous paragraph, a tertiary alcohol can be obtained using a method described herein in with a yield of ≥60%. In some embodiments, including those of the previous paragraph, a tertiary alcohol can be obtained using a method described herein in with a yield of ≥70%. In some embodiments, including those of the previous paragraph, a tertiary alcohol can be obtained using a method described herein in with a yield of ≥80%. In some embodiments, including those of the previous paragraph, a tertiary alcohol can be obtained using a method described herein in with a yield of ≥90%.

Various solvents can be used in a method described herein. For example, the solvent can be hexane, heptane, dichloromethane, toluene and combinations thereof. A variety of temperatures can be also used in a method described herein. In some embodiments, a method described herein can be conducted at a temperature in the range of about −78° C. to about 25° C. In some embodiments, a method described herein can be conducted at a temperature in the range of about −50° C. to about 25° C.

A method described herein can utilize $BF_3 \cdot OEt_2$. The $BF_3 \cdot OEt_2$ can function as a Lewis acid. In some embodiments, the amount of $BF_3 \cdot OEt_2$ used in a method described herein can be present in a catalytic amount. For example, the amount of $BF_3 \cdot OEt_2$ used in a method described herein can be in the range of about 0.05 equivalents to about 1 equivalent relative to 1 equivalent of the optionally substituted phenyl ketone or the optionally substituted pyridinyl ketone ($BF_3 \cdot OEt_2$:optionally substituted phenyl ketone or $BF_3 \cdot OEt_2$:optionally substituted pyridinyl ketone). In some embodiments, the amount of $BF_3 \cdot OEt_2$ used in a method described herein can be in the range of about 0.08 equivalents to about 0.25 equivalent relative to 1 equivalent of the optionally substituted phenyl ketone or the optionally substituted pyridinyl ketone ($BF_3 \cdot OEt_2$:optionally substituted phenyl ketone or $BF_3 \cdot OEt_2$:optionally substituted pyridinyl ketone). In some embodiments, the amount of $BF_3 \cdot OEt_2$ used in a method described herein can be 0.1 equivalent relative to 1 equivalent of the optionally substituted phenyl ketone or the optionally substituted pyridinyl ketone.

Some examples of a tertiary alcohol that can be obtained from a method described herein includes, but are not limited to, the following:

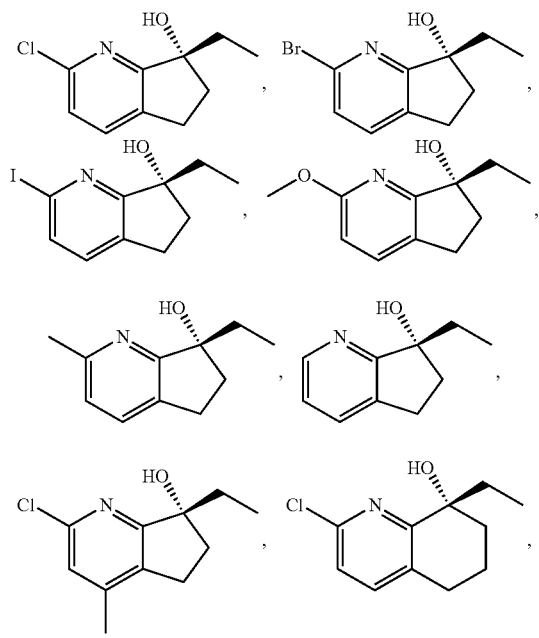

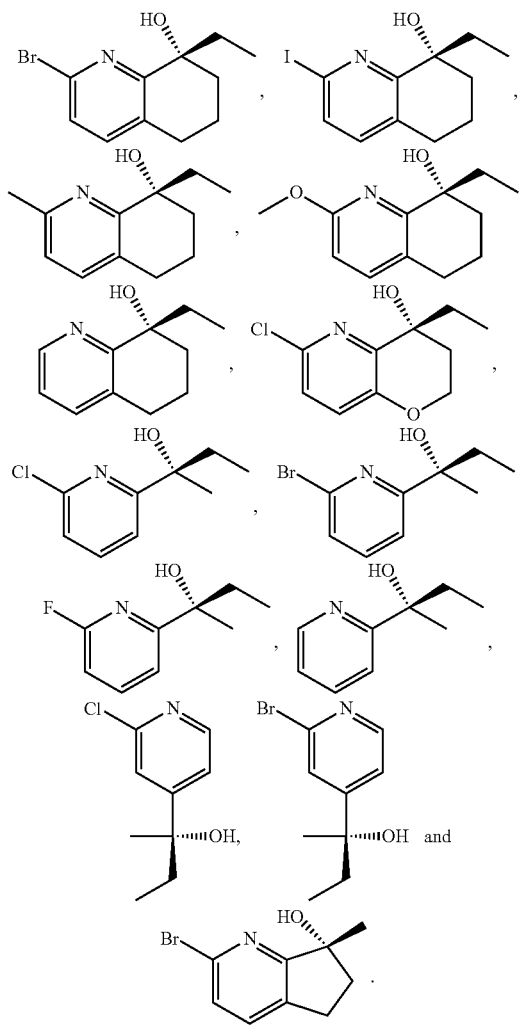

An additional example of a tertiary alcohol that can be obtained by a method described herein includes, but is not limited to, having a structure of a compound of Formula (G1-a):

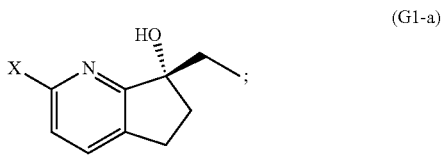

wherein X can be Cl, Br or I. In some embodiments, X can be Cl (chloro). In some embodiments, X can be Br (bromo). In some embodiments, X can be I (iodo).

A compound of Formula (G1-a), wherein X is Cl, can be obtained as various polymorphs, such as Form A and Form B. Various methods can be used to characterize a polymorph of a compound of Formula (G1-a), wherein X is Cl. In some embodiments, Form A can be characterized by one or more peaks in an X-ray powder diffraction pattern, wherein the one or more peaks can be selected from a peak in the range of from about 15.7 degrees 2θ to about 16.7 degrees 2θ, a peak in the range of from about 20.5 degrees 2θ to about 21.5 degrees 2θ, a peak in the range of from about 23.7 degrees 2θ to about 24.7 degrees 2θ and a peak in the range of from about 26.0 degrees 2θ to about 27.0 degrees 2θ. In some embodiments, Form A can be characterized by one or more peaks in an X-ray powder diffraction pattern, wherein the one or more peaks can be selected from about 16.2 degrees 2θ±0.2 degrees 2θ, about 21.0 degrees 2θ±0.2 degrees 2θ, about 24.2 degrees 0.2 degrees 2θ and about 26.5 degrees 2θ±0.2 degrees 2θ. In some embodiments, Form B can be characterized by one or more peaks in an X-ray powder diffraction pattern, wherein the one or more peaks can be selected from a peak in the range of from about 13.5 degrees 2θ to about 14.5 degrees 2θ, a peak in the range of from about 17.1 degrees 2θ to about 18.1 degrees 2θ, a peak in the range of from about 19.6 degrees 2θ to about 20.6 degrees 2θ, a peak in the range of from about 24.3 degrees 2θ to about 25.3 degrees 2θ and a peak in the range of from about 25.0 degrees 2θ to about 26.0 degrees 2θ. In some embodiments, Form B can be characterized by one or more peaks in an X-ray powder diffraction pattern, wherein the one or more peaks can be selected from about 14.0 degrees 2θ±0.2 degrees 2θ, about 17.6 degrees 2θ±0.2 degrees 2θ, about 20.1 degrees 2θ±0.2 degrees 2θ, about 24.8 degrees 2θ±0.2 degrees 2θ and about 25.5 degrees 2θ±0.2 degrees 2θ. In some embodiments, Form A can be characterized by one or more peaks in an X-ray powder diffraction pattern, wherein the one or more peaks can be selected from a peak in Table 5. In some embodiments, Form B can be characterized by one or more peaks in an X-ray powder diffraction pattern, wherein the one or more peaks can be selected from a peak in Table 6. In some embodiments, Form A can exhibit an X-ray powder diffraction pattern as shown in FIG. 1. In some embodiments, Form B can exhibit an X-ray powder diffraction pattern as shown in FIG. 2. All XRPD patterns provided herein are measured on a degrees 2-Theta (2θ) scale. It should be understood that the numerical values of the peaks of an X-ray powder diffraction pattern may vary from one machine to another, or from one sample to another, and so the values quoted are not to be construed as absolute, but with an allowable variability, such as ±0.5 degrees two theta (2θ), or more. For example, in some embodiments, the value of an XRPD peak position may vary by up to ±0.2 degrees 2θ while still describing the particular XRPD peak.

A method described herein for preparing a tertiary alcohol can include the use of $NaHSO_3$ on a tertiary alcohol described herein, such as

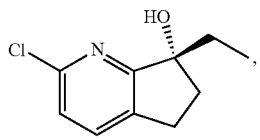

wherein the use of $NaHSO_3$ can increase the enantiomeric excess (ee %) of the tertiary alcohol compared to the ee % prior to the use of $NaHSO_3$. A method described herein can include recrystallization of the tertiary alcohol, including

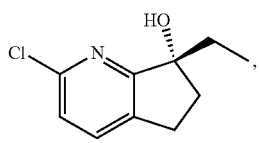

wherein the recrystallization can increase the enantiomeric excess (ee %) of the tertiary alcohol compared to the ee % prior to the recrystallization. In some embodiments, the recrystallization can utilize hexane. In other embodiments, the recrystallization can utilize heptane.

Uses for Compounds

Those skilled in the art recognize that the compounds described herein may be used in various methods to produce compounds of interest. In some embodiments, the compounds described herein may be used to produce compounds that act as WEE1 inhibitors, as WEE1 is found to be overexpressed in various cancer types. Examples of WEE1 inhibitors include those described in PCT Pub. No. WO 2019/173082, published Sep. 12, 2019, which is hereby incorporated herein by reference in its entirety for all purposes. Those skilled in the art recognize that certain compounds described herein may be used as intermediates in the synthesis of WEE1 inhibitors. In some embodiments, the compounds described herein, for example such as compounds of Formula (G1-a), may be used as intermediates in the synthesis of enantiomerically pure or substantially enantiomerically pure WEE1 inhibitors.

EXAMPLES

Additional embodiments are disclosed in further detail in the following examples, which are not in any way intended to limit the scope of the claims.

Example A (R)—N-(3-Methyl-1-(pyrrolidin-1-yl)butan-2-yl)-P,P-diphenylphosphinic amide (63.8 mg, 0.179 mmol) was added to a flame-dried 40 mL vial. The vial was sealed with septa cap, evacuated, filled with $N_2$ (3×) and then cooled to −50° C. 1M Diethylzinc (2.39 mL, 2.39 mmol) in hexanes was added at −50° C., and the mixture was stirred for 30 mins. The Lewis acid (0.1 eq., Table 1) was added, and the mixture was stirred at −50° C. for 30 mins. 2-Chloro-5,6-dihydro-7H-cyclopenta[b]pyridin-7-one (100 mg, 0.597 mmol) in DCM (2.5 mL) was added over 30 mins via syringe pump (5 mL/h). The mixture was stirred for 5 h at −50° C. and then allowed to warm to room temperature (RT) overnight. The mixture was cooled to 0° C., and the reaction was quenched slowly with sat. $NH_4Cl$ (5 mL). The mixture was poured into a mixture of EtOAc (25 mL) and sat. $NH_4Cl$ (25 mL) with stirring. The layers were separated, and the aqueous layer was extracted with EtOAc (2×20 mL). The combined organic layers were washed with brine (1×50 mL) and dried ($Na_2SO_4$). The crude residue was purified by column chromatography ($SiO_2$, EtOAc:hexanes) to afford the alcohol listed below as Example 1. The enantiomeric purity was determined by chiral LCMS. As shown in Table 1, $BF_3 \cdot OEt_2$ showed the best yield and ee % compared to the other listed Lewis acids.

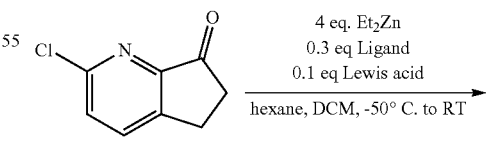

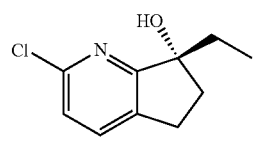

Example 1

-continued

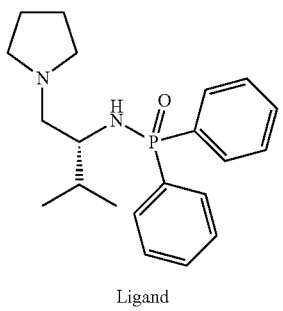

Ligand

TABLE 1

| Lewis Acid | ee % | Yield |
|---|---|---|
| BF$_3$·OEt$_2$ | 95% | 77% |
| B(OEt)$_3$ | 62% | 51% |
| Ti(OiPr)$_4$ | 16% | 46% |
| ZnCl$_2$ | 55% | 31% |
| LiBF$_4$ | 53% | 28% |
| TiCl$_4$ | 73% | 18% |

Example B (R)—N-(3-Methyl-1-(pyrrolidin-1-yl)butan-2-yl)-P,P-diphenylphosphinic amide (63.8 mg, 0.179 mmol) was added to a flame dried 40 mL vial. The vial was sealed with septa cap, evacuated, filled with N$_2$ (3×) and then cooled to −78° C. 1M Diethylzinc (2.98 mL, 2.98 mmol) in hexanes was added at −78° C., and the mixture was stirred for 30 mins. To this mixture was added BF$_3$.OEt$_2$ (see Table 2) via syringe, and the mixture was stirred at −78° C. for 30 mins. 2-Chloro-5,6-dihydro-7H-cyclopenta[b]pyridin-7-one (100 mg, 0.597 mmol) in DCM (2.5 mL) was added at −78° C. using a syringe pump over 30 mins (5 mL/h). The mixture was stirred for 2 h at −78° C., slowly warmed to RT and then stirred for 20 h. The mixture was cooled to 0° C., and the reaction was quenched by slowly adding sat. NH$_4$Cl (5 mL) with stirring. The reaction was poured into a mixture of EtOAc (20 mL) and sat. NH$_4$Cl (20 mL) with stirring. The layers were separated, and the aqueous layer was extracted with EtOAc (2×25 mL). The combined organic layers were washed with brine (1×50 mL) and dried (Na$_2$SO$_4$). The solvent was evaporated, and the crude residue was analyzed by chiral LCMS. As shown in Table 2, 0.1 equivalents of BF$_3$.OEt$_2$ provided the highest ee %.

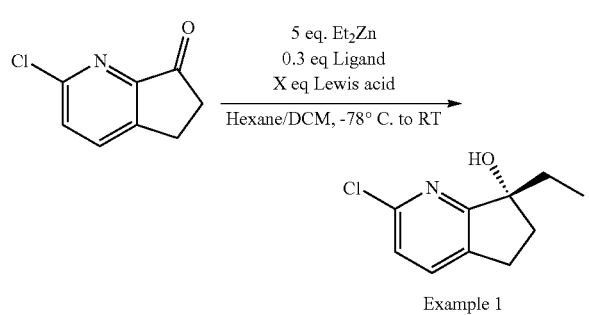

Example 1

-continued

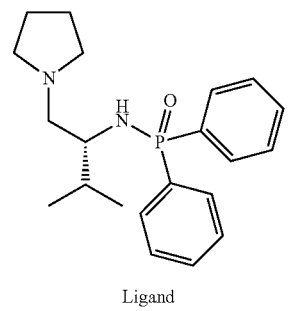

Ligand

TABLE 2

| Entry | BF$_3$·OEt$_2$ (eq) | Ketone Remaining | ee % |
|---|---|---|---|
| 1 | 1 | 4% | 20% |
| 2 | 0.8 | 2.5% | 42% |
| 3 | 0.6 | 2% | 46% |
| 4 | 0.4 | 2% | 70% |
| 5 | 0.2 | 1.5% | 80% |
| 6 | 0.1 | 8% | 94% |
| 7 | 0 | 47% | 40% |

Example C

The ligand (0.3 eq, Table 3) was added to a flame dried 40 mL vial. The vial was sealed with septa cap, evacuated, filled with N$_2$ (3×) and then cooled to −50° C. 1M Diethylzinc (2.39 mL, 2.39 mmol) in hexanes was added at −50° C., and the mixture was stirred for 30 min. To this mixture was added a BF$_3$.OEt$_2$ solution [100 μL, prepared by diluting 70 μL of BF$_3$.OEt$_2$ (0.007 mL, 0.060 mmol) in 930 μL of DCM], and the mixture was stirred for 30 mins at −50° C. 2-Chloro-5,6-dihydro-7H-cyclopenta[b]pyridin-7-one (100 mg, 0.597 mmol) in DCM (2.5 mL) was added at −50° C. using a syringe pump over 30 mins (5 mL/h). The mixture was stirred for 5 h at −50° C., slowly warmed to RT and then stirred for 20 h. The mixture was cooled to 0° C., and the reaction was quenched by slowly adding sat. NH$_4$Cl (5 mL) with stirring. The reaction was poured into a mixture of EtOAc (20 mL) and sat. NH$_4$Cl (20 mL) with stirring. The layers were separated, and the aqueous layer was extracted with EtOAc (2×25 mL). The combined organic layers were washed with brine (1×50 mL) and dried (Na$_2$SO$_4$). The solvent was evaporated, and the crude residue was analyzed by chiral LCMS. Ligand 1 provides high ee % and ≤10% remaining of the starting ketone. Ligands 4 and 5 provide high ee % and ≤20% remaining of the starting ketone.

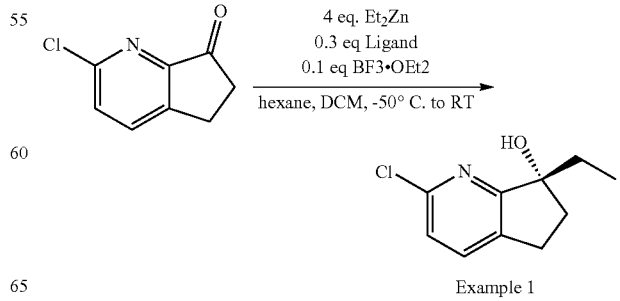

Example 1

TABLE 3

| Entry | Ligand (0.3 eq) | BF₃OEt₂ (eq) | Temp. | Ketone Remaining | Ena 1:Ena 2 | ee |
|---|---|---|---|---|---|---|
| 1 | (pyrrolidine-CH₂-CH(iPr)-NH-P(=O)Ph₂) | 0.1 | −50° C. (5 h) to RT | 10% | 97.7:2.2 | 95.5% |
| 2 | (trans-cyclohexane-1,2-diyl with pyrrolidine and HN-P(=O)Ph₂) | 0.1 | −50° C. (5 h) to RT | 56% | 27:72 | 45% |
| 3 | (pyrrolidine-CH₂-CH(iPr)-NH-P(=O)(o-tolyl)₂) | 0.1 | −50° C. (5 h) to RT | 23% | 95:5 | 90% |
| 4 | (pyrrolidine-CH₂-CH(iPr)-NH-P(=O)(4-MeOC₆H₄)₂) | 0.1 | −50° C. (5 h) to RT | 20% | 98.5:1.5 | 97% |
| 5 | (pyrrolidine-CH₂-CH(Et)-NH-P(=O)Ph₂) | 0.1 | −50° C. (5 h) to RT | 18% | 97.2:2.8 | 94.4% |

TABLE 3-continued

| Entry | Ligand (0.3 eq) | BF$_3$OEt$_2$ (eq) | Temp. | Ketone Remaining | Ena 1:Ena 2 | ee |
|---|---|---|---|---|---|---|
| 6 | | 0.1 | −50° C. (5 h) to RT | 38% | 94:6 | 88% |
| 7 | | 0.1 | −50° C. (5 h) to RT | 26% | 93:7 | 86% |
| 8 | | 0.4 | −78° C. (5 h) to RT | 4.7% | 78:22 | 56% |
| 9 | | 0.4 | −78° C. (5 h) to RT | overlapped | 65:35 | 30% |

Solvent was DCM for each entry

Ena 1 has the structure 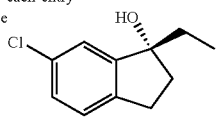 ;

and Ena 2 has the structure 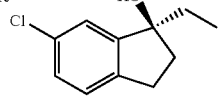.

General Procedure for Examples 1-21

(R)—N-(3-Methyl-1-(pyrrolidin-1-yl)butan-2-yl)-P,P-diphenylphosphinic amide (0.160 g, 0.450 mmol) was added to a flame-dried 40 mL vial. The vial was sealed with septa cap, evacuated, filled with N$_2$ (3×) and then cooled to −50° C. 1M diethylzinc (6.00 mL, 6.00 mmol) in hexanes was added, and the mixture was stirred for 30 mins. A BF$_3$.OEt$_2$ solution [100 μL, prepared by diluting 190 μL of BF$_3$.OEt$_2$ (0.019 mL, 0.150 mmol) in 810 μL of DCM] was added to the reaction, and the mixture was stirred for 30 mins at −50° C. The ketone (1.5 mmol) in DCM (2.5 mL) was added over 30 mins via a syringe pump. The mixture was stirred for 5 h at −50° C. and then allowed to warm to RT overnight. The mixture was cooled to 0° C., and the reaction was quenched slowly with sat. NH₄Cl (5 mL). The mixture was poured into a mixture of EtOAc (25 mL) and sat. NH₄Cl (25 mL) with stirring. The layers were separated, and the aqueous layer was extracted with EtOAc (2×20 mL). The combined organic layers were washed with brine (1×75 mL) and dried (Na₂SO₄). The crude residue was purified by column chromatography (SiO₂, EtOAc:hexanes) to afford the desired alcohol. The enantiomeric purity was determined by chiral LCMS, HPLC or chiral SFC. The absolute stereochemistry for Example 1 was determined by X-ray crystallography of a later compound in a synthesis provided in WO 2019/173082. The absolute stereochemistry of Examples 2-21 is arbitrarily assigned.

Example 1

(R)-2-Chloro-7-ethyl-6,7-dihydro-5H-cyclopenta[b]pyridin-7-ol

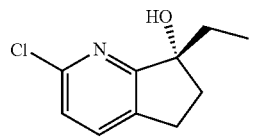

Example 1: 908 mg, (77%), a colorless oil. ¹H NMR (400 MHz, CDCl₃) δ 7.50 (d, J=7.9 Hz, 1H), 7.17 (d, J=8.1 Hz, 1H), 2.99-2.90 (m, 1H), 2.82-2.71 (m, 1H), 2.33 (ddd, J=4.3, 8.7, 13.4 Hz, 1H), 2.19 (ddd, J=6.8, 9.0, 13.5 Hz, 1H), 2.04-1.89 (m, 1H), 1.81 (qd, J=7.3, 14.1 Hz, 1H), 0.94 (t, J=7.5 Hz, 3H). ¹³C NMR (101 MHz, CDCl₃) δ 166.90, 150.07, 135.67, 134.94, 123.10, 81.98, 36.03, 32.37, 26.47, 8.13. LCMS (APCI) m/z 198.1 [M+H]⁺. 97% ee; Chiral analysis was done by LCMS on a Lux Cellulose-4 column (4.6×150), which was eluted by CH₃CN/Water 0.1% formic acid at 1.2 mL/min. Under the conditions, Example 1 eluted as peak 1 ($t_1$=8.16 min), and the enantiomer was eluted as peak 2 ($t_1$=8.54 min). As provided in WO 2019/173082, the compound of Example 1 can be used to prepare a compound that has been shown to inhibit the activity of WEE1 in a cell, and therefore, can be effective as an anti-cancer agent.

Example 2

(R)-2-Bromo-7-ethyl-6,7-dihydro-5H-cyclopenta[b]pyridin-7-ol

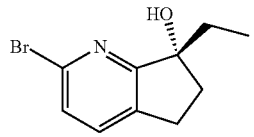

Example 2: 235 mg (65%) a colorless oil. ¹H NMR (400 MHz, CDCl₃) δ 7.41 (d, J=7.9 Hz, 1H), 7.32 (d, J=7.9 Hz, 1H), 2.98-2.89 (m, 1H), 2.80-2.71 (m, 1H), 2.36-2.29 (m, 2H), 2.22-2.21 (m, 1H), 2.02-1.92 (m, 1H), 1.86-1.76 (m, 1H), 0.95 (t, J=7.5 Hz, 3H). ¹³C NMR (101 MHz, CDCl₃) δ 167.65, 140.74, 135.51, 135.27, 126.89, 82.02, 35.95, 32.49, 26.56, 8.16. LCMS (APCI) m/z 242.7 [M+H]⁺. 96.4% ee. Chiral analysis was done by LCMS on a Lux Cellulose-4 column (4.6×150 mm), which was eluted by CH₃CN/Water 0.1% formic acid at 1.2 mL/min. Under the conditions, Example 2 eluted as peak 1 ($t_1$=8.73 min), and the enantiomer eluted as peak 2 ($t_1$=9.17 min).

Example 3

(R)-7-Ethyl-2-iodo-6,7-dihydro-5H-cyclopenta[b]pyridin-7-ol

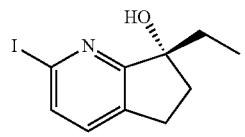

Example 3:114 mg (32%), a colorless oil. ¹H NMR (400 MHz, CDCl₃) δ 7.54 (d, J=7.8 Hz, 1H), 7.20 (d, J=7.8 Hz, 1H), 2.96-2.87 (m, 1H), 2.78-2.68 (m, 1H), 2.42 (br s, 1H), 2.29 (ddd, J=4.2, 8.7, 13.3 Hz, 1H), 2.15 (ddd, J=7.0, 9.0, 13.5 Hz, 1H), 2.04-1.87 (m, 1H), 1.83-1.73 (m, 1H), 0.94 (t, J=7.5 Hz, 3H). ¹³C NMR (101 MHz, CDCl₃) δ 168.53, 135.66, 134.78, 133.50, 115.94, 81.93, 35.75, 32.38, 26.58, 8.13. LCMS (APCI) m/z 290.0 [M+H]⁺. 92% ee; Chiral analysis was done by LCMS on a Lux Cellulose-4 column (4.6×150 mm), which was eluted by CH₃CN/Water 0.1% formic acid at 1.2 mL/min. Under the conditions, Example 3 eluted as peak 1 ($t_1$=9.63 min), and the enantiomer eluted as peak 2 ($t_2$=10.09 min).

Example 4

(R)-7-Ethyl-2-methoxy-6,7-dihydro-5H-cyclopenta[b]pyridin-7-ol

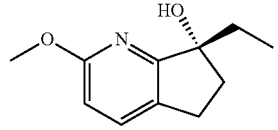

Example 4: 80 mg (27%), a colorless oil. ¹H NMR (400 MHz, CDCl₃) δ 7.43 (d, J=8.3 Hz, 1H), 6.60 (d, J=8.3 Hz, 1H), 3.94 (s, 3H), 2.88 (ddd, J=3.9, 9.0, 15.7 Hz, 1H), 2.71 (td, J=7.7, 15.5 Hz, 1H), 2.33 (ddd, J=4.0, 8.3, 13.4 Hz, 2H), 2.23-2.10 (m, 1H), 2.00-1.87 (m, 1H), 1.84-1.74 (m, 1H), 0.96 (t, J=7.5 Hz, 3H). ¹³C NMR (101 MHz, CDCl₃) δ 164.38, 162.83, 135.63, 127.84, 109.68, 82.16, 53.41, 36.64, 32.48, 26.31, 8.22. LCMS (APCI) m/z 194.0 [M+H]. 96.7% ee, Chiral analysis was done by chiral SFC on a Chiralpak IG-3 column (4.6×150 mm), which was eluted by 10% (0.5% DEA in methanol) at 3 g/min at 30° C. Under these conditions, the enantiomer eluted as peak 1 ($t_1$=1.45 min), and Example 4 eluted as peak 2 ($t_1$=1.83 min).

Example 5

(R)-7-Ethyl-2-methyl-6,7-dihydro-5H-cyclopenta[b]pyridin-7-ol

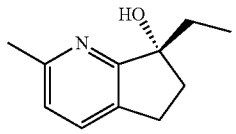

Example 5: 55 mg (23%), a colorless oil. $^1$H NMR (400 MHz, CDCl$_3$) δ 7.42 (d, J=7.8 Hz, 1H), 6.99 (d, J=7.8 Hz, 1H), 2.92 (ddd, J=3.8, 9.1, 16.1 Hz, 1H), 2.81-2.69 (m, 1H), 2.66 (s, 1H), 2.56-2.53 (m, 3H), 2.33 (ddd, J=3.9, 8.3, 13.4 Hz, 1H), 2.15 (ddd, J=7.3, 9.0, 13.4 Hz, 1H), 2.05-1.89 (m, 1H), 1.86-1.74 (m, 1H), 0.95 (t, J=7.5 Hz, 3H). $^{13}$C NMR (101 MHz, CDCl$_3$) δ 165.47, 156.77, 133.19, 132.87, 122.24, 82.02, 36.34, 32.51, 26.64, 23.83, 8.24. LCMS (APCI) m/z 178.0 [M+H]$^+$. 93.0% ee, Chiral analysis was done by Chiral SFC on a Chiralpak IF-3 column (4.6×150 mm), which was eluted by 15% (0.5% DEA in methanol) at 3 g/min at 30° C. Under these conditions, the enantiomer eluted as peak 1 ($t_1$=1.23 min), and Example 5 eluted as peak 2 ($t_1$=1.40 min).

Example 6

(R)-7-Ethyl-6,7-dihydro-5H-cyclopenta[b]pyridin-7-ol

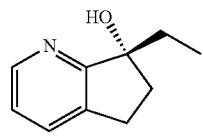

Example 6: 47 mg (19%), a colorless oil. $^1$H NMR (400 MHz, CDCl$_3$) δ 8.47-8.42 (m, 1H), 7.55 (dd, J=1.2, 7.6 Hz, 1H), 7.14 (dd, J=4.9, 7.6 Hz, 1H), 3.04-2.93 (m, 1H), 2.86-2.76 (m, 1H), 2.37-2.30 (m, 1H), 2.30-2.11 (m, 1H), 2.05-1.91 (m, 1H), 1.91-1.79 (m, 1H), 0.99-0.93 (m, 3H). $^{13}$C NMR (101 MHz, CDCl$_3$) δ 166.14, 147.96, 136.21, 133.14, 122.64, 82.04, 36.10, 32.55, 27.03, 8.30. LCMS (APCI) m/z 164.6 [M+H]$^+$. 80% ee, Chiral analysis was done by chiral SFC on a Chiralpak AD-3 column (4.6×150 mm), which was eluted by 10% (0.5% DEA in methanol) at 3 g/min at 30° C. Under these conditions, the enantiomer eluted as peak 1 ($t_1$=1.71 min), and Example 6 eluted as peak 2 ($t_1$=2.44 min).

Example 7

(R)-2-Chloro-7-ethyl-4-methyl-6,7-dihydro-5H-cyclopenta[b]pyridin-7-ol

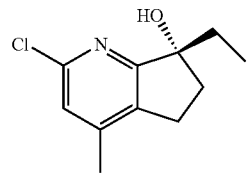

Example 7: 219 mg (69%), a colorless oil. $^1$H NMR (400 MHz, CDCl$_3$) δ 7.01 (s, 1H), 2.87 (ddd, J=4.3, 9.1, 16.4 Hz, 1H), 2.71-2.62 (m, 1H), 2.41-2.30 (m, 1H), 2.26 (s, 3H), 2.24-2.13 (m, 1H), 2.04-1.88 (m, 1H), 1.85-1.71 (m, 1H), 0.92 (t, J=7.5 Hz, 3H). $^{13}$C NMR (101 MHz, CDCl$_3$) δ 166.00, 150.35, 147.14, 134.41, 123.67, 82.24, 35.51, 32.62, 25.20, 18.47, 8.24. LCMS (APCI) m/z 212.7 [M+H]$^+$. 92% ee; Chiral analysis was done by LCMS on a Lux Cellulose-4 column (4.6×150 mm), which was eluted by CH$_3$CN/Water 0.1% formic acid at 1.2 mL/min. Under the conditions, Example 7 eluted as peak 1 ($t_1$=9.43 min), and the enantiomer eluted as peak 2 ($t_2$=9.77 min).

Example 8

(R)-2-Bromo-7-ethyl-6,7-dihydro-5H-cyclopenta[b]pyridin-7-ol

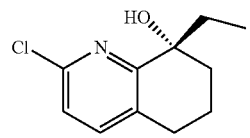

Example 8: 175 mg (60%), a colorless oil. $^1$H NMR (400 MHz, CDCl$_3$) δ 7.35 (d, J=7.8 Hz, 1H), 7.11 (d, J=8.1 Hz, 1H), 3.04 (br s, 1H), 2.84-2.66 (m, 2H), 2.12-1.96 (m, 1H), 1.96-1.62 (m, 5H), 0.93 (t, J=7.5 Hz, 3H). $^{13}$C NMR (101 MHz, CDCl$_3$) δ 161.65, 148.44, 139.73, 130.02, 122.66, 72.58, 34.22, 32.09, 28.07, 18.98, 7.68. LCMS (APCI) m/z 212.1 [M+H]$^+$. 88% ee; Chiral analysis was done by LCMS on a Lux Cellulose-4 column (4.6×150 mm), which was eluted by CH$_3$CN/Water 0.1% formic acid at 1.2 mL/min. Under the conditions, Example 8 eluted as peak 1 ($t_1$=10.41 min), and the enantiomer eluted as peak 2 ($t_2$=10.75 min).

Example 9

(R)-2-Bromo-8-ethyl-5,6,7,8-tetrahydroquinolin-8-ol

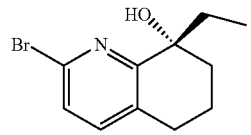

Example 9: 193 mg (50%), a colorless oil. $^1$H NMR (400 MHz, CDCl$_3$) δ 7.26 (s, 2H), 3.06 (s, 1H), 2.81-2.67 (m, 2H), 2.13-2.03 (m, 1H), 1.95-1.75 (m, 5H), 0.94 (t, J=7.5 Hz, 3H). $^{13}$C NMR (101 MHz, CDCl$_3$) δ=162.44, 139.46, 138.92, 130.42, 126.43, 72.59, 34.25, 32.04, 28.11, 18.93, 7.67. LCMS (APCI) m/z 256.7 [M+H]$^+$. 85% ee, Chiral analysis was done by LCMS on a Lux Cellulose-4 column (4.6×150 mm), which was eluted by CH$_3$CN/Water 0.1% formic acid at 1.2 mL/min. Under the conditions, Example 9 eluted as peak 1 (t$_1$=10.9 min), and the enantiomer eluted as peak 2 (t$_1$=11.3 min).

Example 10

(R)-8-Ethyl-2-iodo-5,6,7,8-tetrahydroquinolin-8-ol

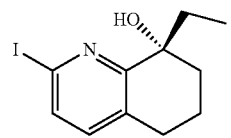

Example 10: 298 mg (66%), a colorless oil. $^1$H NMR (400 MHz, CDCl$_3$) δ 7.52-7.46 (m, 1H), 7.05-6.99 (m, 1H), 3.15 (s, 1H), 2.79-2.65 (m, 2H), 2.17-1.71 (m, 6H), 0.93 (t, J=7.4 Hz, 3H). LCMS (APCI) m/z 304.0 [M+H]$^+$. 71% ee; Chiral analysis was done by LCMS on a Lux Cellulose-4 column (4.6×150 mm), which was eluted by CH$_3$CN/Water 0.1% formic acid at 1.2 mL/min. Under the conditions, Example 10 eluted as peak 1 (t$_1$=11.79 min), and the enantiomer eluted as peak 2 (t$_2$=12.12 min).

Example 11

(R)-8-Ethyl-2-methyl-5,6,7,8-tetrahydroquinolin-8-ol

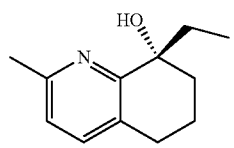

Example 11: 117 mg (41%), a colorless oil. $^1$H NMR (400 MHz, CDCl$_3$) δ 7.27 (d, J=8.0 Hz, 1H), 6.94 (d, J=7.8 Hz, 1H), 3.76 (s, 1H), 2.81-2.69 (m, 2H), 2.49 (s, 3H), 2.20-2.10 (m, 1H), 1.93-1.73 (m, 5H), 0.94 (t, J=7.4 Hz, 3H). $^{13}$C NMR (101 MHz, CDCl$_3$) δ 160.03, 155.16, 136.98, 127.35, 121.61, 72.29, 34.24, 32.30, 27.91, 23.93, 19.16, 7.67. LCMS (APCI) m/z 192.0 [M+H]$^+$. 84.6% ee, Chiral analysis was done by chiral SFC on a Chiralpak IG-3 column (4.6×150 mm), which was eluted by 10% (0.5% DEA in methanol) at 3 g/min at 30° C. Under these conditions, the enantiomer eluted as peak 1 (t$_1$=1.98 min), and Example 11 eluted as peak 2 (t$_1$=2.46 min).

Example 12

(R)-8-Ethyl-2-methoxy-5,6,7,8-tetrahydroquinolin-8-ol

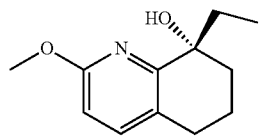

Example 12: 150 mg (48%), a colorless oil. $^1$H NMR (400 MHz, CDCl$_3$) δ 7.29 (d, J=8.4 Hz, 1H), 6.57 (d, J=8.3 Hz, 1H), 3.92 (s, 3H), 3.28 (s, 1H), 2.76-2.63 (m, 2H), 2.14-2.04 (m, 1H), 1.92-1.73 (m, 5H), 0.94 (t, J=7.5 Hz, 3H). $^{13}$C NMR (101 MHz, CDCl$_3$) δ 162.05, 157.15, 139.93, 123.13, 109.38, 72.46, 53.16, 34.21, 32.41, 27.59, 19.32, 7.83. LCMS (APCI) m/z 208.0 [M+H]$^+$. 90.0% ee, Chiral analysis was done by chiral SFC on a Chiralpak AD-3 column (4.6×150 mm), which was eluted by 15% (0.5% DEA in methanol) at 3 g/min at 30° C. Under these conditions, the enantiomer eluted as peak 1 (t$_1$=1.31 min), and Example 12 eluted as peak 2 (t$_1$=1.47 min).

Example 13

(R)-8-Ethyl-5,6,7,8-tetrahydroquinolin-8-ol

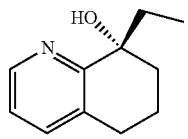

Example 13: 81 mg (30%), a colorless oil. $^1$H NMR (400 MHz, CDCl$_3$) δ 8.40 (d, J=4.8 Hz, 1H), 7.40 (d, J=7.7 Hz, 1H), 7.10 (dd, J=4.8, 7.7 Hz, 1H), 3.52 (s, 1H), 2.87-2.74 (m, 2H), 2.23-2.01 (m, 1H), 1.99-1.75 (m, 5H), 0.93 (t, J=7.4 Hz, 3H). $^{13}$C NMR (101 MHz, CDCl$_3$) δ 160.89, 146.51, 136.92, 131.21, 122.10, 72.53, 34.35, 32.43, 28.50, 19.06, 7.77. LCMS (APCI) m/z 178.7 [M+H]$^+$. 74% ee; Chiral analysis was done by chiral SFC on a CHIRALPAK IG-3 column (4.6×150 mm), which was eluted by 15% (0.5% DEA in methanol) at 3 g/min. Under the conditions, Example 13 eluted as peak 1 (t$_1$=2.35 min), and the enantiomer eluted as peak 2 (t$_2$=3.07 min).

Example 14

(R)-6-Chloro-4-ethyl-3,4-dihydro-2H-pyrano[3,2-b]pyridin-4-ol

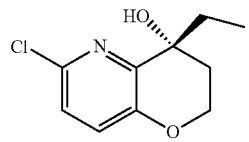

Example 14: 122 mg (38%) a colorless oil. $^1$H NMR (400 MHz, CDCl$_3$) δ 7.11 (d, J=1.5 Hz, 2H), 4.31-4.20 (m, 2H), 2.52 (br s, 1H), 2.20-2.01 (m, 3H), 1.88 (qd, J=7.4, 14.4 Hz, 1H), 0.93 (t, J=7.5 Hz, 3H). LCMS (APCI) m/z 214.1 [M+H]$^+$. 79% ee; Chiral analysis was done by LCMS on a Lux Cellulose-4 column (4.6×150 mm), which was eluted by CH$_3$CN/Water 0.1% formic acid at 1.2 mL/min. Under the conditions, Example 14 eluted as peak 1 (t$_1$=6.85 min), and the enantiomer eluted as peak 2 (t$_2$=7.04 min).

Example 15

(S)-2-(6-Chloropyridin-2-yl)butan-2-ol

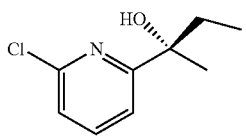

Example 15: 218 mg (78%), a colorless oil. $^1$H NMR (400 MHz, CDCl$_3$) δ 7.66 (t, J=7.8 Hz, 1H), 7.28-7.26 (m, 1H), 7.22 (dd, J=0.6, 7.8 Hz, 1H), 1.88-1.66 (m, 2H), 1.52 (s, 3H), 0.77 (t, J=7.5 Hz, 3H). $^{13}$C NMR (101 MHz, CDCl$_3$) δ 166.60, 149.83, 139.42, 122.22, 117.76, 74.35, 35.90, 28.49, 8.03. LCMS (APCI) m/z 186.1 [M+H]$^+$. 40% ee; Chiral analysis was done by chiral SFC on a CHIRALPAK IG-3 (4.6×150 mm), which was eluted by 15% (0.5% DEA in methanol) at 3 g/min. Under the conditions, Example 15 eluted as peak 1 (t$_1$=1.25 min), and the enantiomer eluted as peak 2 (t$_2$=1.51 min).

Example 16

(S)-2-(6-Bromopyridin-2-yl)butan-2-ol

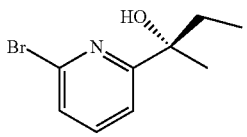

Example 16: 229 mg (66%), a colorless oil, $^1$H NMR (400 MHz, CDCl$_3$) δ 7.59-7.53 (m, 1H), 7.38 (dd, J=0.7, 7.8 Hz, 1H), 7.31 (dd, J=0.6, 7.7 Hz, 1H), 4.19 (s, 1H), 1.83 (dq, J=1.5, 7.4 Hz, 2H), 1.51 (s, 3H), 0.78 (t, J=7.5 Hz, 3H). $^{13}$C NMR (101 MHz, CDCl$_3$) δ 167.09, 140.40, 139.08, 126.00, 118.08, 74.28, 35.86, 28.42, 7.99. LCMS (APCI) m/z 230.6 [M+H]$^+$. 84% ee, Chiral analysis was done by chiral SFC on a Chiralpak IG-3 column (4.6×150 mm), which was eluted by 20% (0.5% DEA in methanol) at 3 g/min at 30° C. Under these conditions, Example 16 eluted as peak 1 (t$_1$=1.44 min), and the enantiomer eluted as peak 2 (t$_1$=1.76 min).

Example 17

(S)-2-(6-Fluoropyridin-2-yl)butan-2-ol

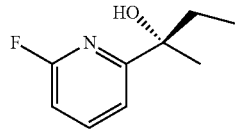

Example 17: 111 mg (44%), a colorless oil. $^1$H NMR (400 MHz, CDCl$_3$) δ 7.80 (q, J=7.9 Hz, 1H), 7.27-7.24 (m, 1H), 6.82 (dd, J=2.7, 8.1 Hz, 1H), 1.89-1.80 (m, 2H), 1.53 (s, 3H), 0.78 (t, J=7.5 Hz, 3H). $^{13}$C NMR (101 MHz, CDCl$_3$) δ 165.09 (d, J=10.3 Hz), 162.42 (d, J=241.4 Hz), 141.72 (d, J=7.3 Hz), 116.40 (d, J=4.4 Hz), 107.06 (d, J=35.9 Hz), 74.38, 35.83, 28.31, 7.97. LCMS (APCI) m/z 170.0 [M+H]$^+$. 54% ee, Chiral analysis was done by chiral SFC on a Chiralpak IF-3 column (4.6×150 mm), which was eluted by 10% methanol at 3 g/min at 30° C. Under these conditions, Example 17 eluted as peak 1 (t$_1$=1.13 min), and the enantiomer was eluted as peak 2 (t$_1$=1.31 min).

Example 18

(S)-2-(Pyridin-2-yl)butan-2-ol

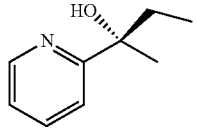

Example 18: 116 mg (51%), a colorless oil. $^1$H NMR (400 MHz, CDCl$_3$) δ 8.51 (td, J=0.8, 4.9 Hz, 1H), 7.70 (dt, J=1.7, 7.7 Hz, 1H), 7.31 (d, J=7.9 Hz, 1H), 7.19 (ddd, J=1.0, 4.9, 7.5 Hz, 1H), 5.17 (br s, 1H), 1.90-1.55 (m, 2H), 1.50 (s, 3H), 0.73 (t, J=7.4 Hz, 3H). $^{13}$C NMR (101 MHz, CDCl$_3$) δ 164.79, 147.14, 136.89, 121.69, 119.23, 73.85, 36.02, 28.81, 7.97. LCMS (APCI) m/z 152.6 [M+H]$^+$. 30% ee, Chiral analysis was done by chiral SFC on a CHIRALPAK AD-3 column (4.6×150 mm), which was eluted by 20% (0.5% DEA in methanol) in methanol at 3 g/min. Under the conditions, Example 18 eluted as peak 1 (t$_1$=1.17 min), and the enantiomer eluted as peak 2 (t$_2$=1.32 min).

Example 19

(S)-2-(2-Chloropyridin-4-yl)butan-2-ol

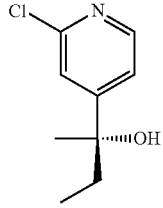

Example 19: 139 mg (50%), a colorless oil. $^1$H NMR (400 MHz, CDCl$_3$) δ 8.33 (d, J=5.3 Hz, 1H), 7.41 (d, J=1.6 Hz, 1H), 7.26 (s, 1H), 7.24 (dd, J=1.6, 5.3 Hz, 1H), 1.88-1.74 (m, 2H), 1.53 (s, 3H), 0.81 (t, J=7.5 Hz, 3H). $^{13}$C NMR (101 MHz, CDCl$_3$) δ 160.52, 151.68, 149.26, 120.97, 119.20, 74.19, 36.18, 29.34, 7.89. LCMS (APCI) m/z 186.1 [M+H]$^+$. 75% ee; Chiral analysis was done by chiral HPLC on a CHIRALPAK IF column (4.6×250 mm), using ethanol and n-hexanes as eluents at 1.0 mL/min. Under the conditions, Example 19 eluted as peak 1 (t$_1$=9.78 min), and the enantiomer eluted as peak 2 (t$_2$=10.28 min).

Example 20

(S)-2-(2-Bromopyridin-4-yl)butan-2-ol

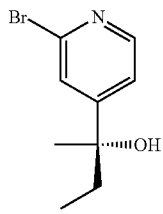

Example 20: 170 mg (49%), a white solid. $^1$H NMR (400 MHz, CDCl$_3$) δ 8.31 (d, J=5.3 Hz, 1H), 7.58 (d, J=1.6 Hz, 1H), 7.28 (dd, J=1.6, 5.3 Hz, 1H), 1.87-1.76 (m, 2H), 1.53 (s, 3H), 0.82 (t, J=7.5 Hz, 3H). $^{13}$C NMR (101 MHz, CDCl$_3$) δ 160.06, 149.82, 142.52, 124.74, 119.54, 74.19, 36.21, 29.42, 7.91. LCMS (APCI) m/z 230.6 [M+H]$^+$. 80% ee, Chiral analysis was done by chiral HPLC on a Lux Cellulose-4 column (4.6×150 mm), which was eluted by CH$_3$CN/Water 0.1% formic acid at 1.2 mL/min. Under the conditions, Example 20 eluted as peak 1 (t$_1$=6.56 min), and the enantiomer eluted as peak 2 (t$_1$=6.75 min).

Example 21

(R)-2-Bromo-7-methyl-6,7-dihydro-5H-cyclopenta[b]pyridin-7-ol

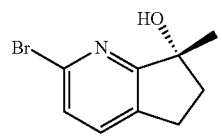

Example 21: This reaction was carried out according to the general procedure using 10% Me$_2$Zn in place of Et$_2$Zn. 54 mg (16%), a white solid. $^1$H NMR (400 MHz, CDCl$_3$) δ 7.42 (td, J=0.9, 7.9 Hz, 1H), 7.33 (d, J=7.9 Hz, 1H), 2.99-2.90 (m, 1H), 2.81-2.69 (m, 1H), 2.34-2.18 (m, 2H), 1.59 (s, 3H). $^{13}$C NMR (101 MHz, CDCl$_3$) δ 168.09, 140.69, 135.66, 134.61, 126.89, 79.27, 39.27, 26.69, 26.33. LCMS (APCI) m/z 227.9 [M+H]$^+$. 94% ee, Chiral analysis was done by LCMS on a Lux Cellulose-4 column (4.6×150 mm), which was eluted by CH$_3$CN/Water 0.1% formic acid at 1.2 mL/min. Under the conditions, Example 21 eluted as peak 1 (t$_1$=7.49 min), and the enantiomer eluted as peak 2 (t$_1$=7.78 min).

TABLE 4

| Ex. | Alcohol | ee % | Yield % |
|---|---|---|---|
| 1 | (2-Cl pyridine cyclopentyl Et alcohol) | 97 | 77 |
| 2 | (2-Br pyridine cyclopentyl Et alcohol) | 96 | 65 |
| 3 | (2-I pyridine cyclopentyl Et alcohol) | 92 | 32 |
| 4 | (2-OMe pyridine cyclopentyl Et alcohol) | 97 | 27 |
| 5 | (2-Me pyridine cyclopentyl Et alcohol) | 93 | 23 |
| 6 | (pyridine cyclopentyl Et alcohol) | 80 | 19 |
| 7 | (2-Cl-4-Me pyridine cyclopentyl Et alcohol) | 92 | 69 |
| 8 | (2-Cl pyridine cyclohexyl Et alcohol) | 88 | 60 |
| 9 | (2-Br pyridine cyclohexyl Et alcohol) | 85 | 50 |
| 10 | (2-I pyridine cyclohexyl Et alcohol) | 71 | 66 |

TABLE 4-continued

| Ex. | Alcohol | ee % | Yield % |
|---|---|---|---|
| 11 | (structure) | 85 | 41 |
| 12 | (structure) | 90 | 48 |
| 13 | (structure) | 74 | 30 |
| 14 | (structure) | 79 | 38 |
| 15 | (structure) | 40 | 78 |
| 16 | (structure) | 84 | 66 |
| 17 | (structure) | 54 | 44 |
| 18 | (structure) | 30 | 51 |
| 19 | (structure) | 75 | 50 |
| 20 | (structure) | 80 | 49 |
| 21 | (structure) | 94 | 16 |

As shown in Table 4, methods described herein can be used to prepare tertiary alcohols with high yield, high enantiomeric purity and/or both. Further, as described herein, tertiary alcohols can be used in the preparation of synthetic versions of natural products and pharmaceuticals.

Example D

Scale-up synthesis of (R)-2-Chloro-7-ethyl-6,7-dihydro-5H-cyclopenta[b]pyridin-7-ol (R)—N-(3-Methyl-1-(pyrrolidin-1-yl)butan-2-yl)-P,P-diphenylphosphinic amide (16.0 kg, 44.9 mol) was suspended in n-heptane (125 L, 5V) in a 1000 L reactor under $N_2$. The suspension was cooled to an internal temperature of –65° C. 2.0 M Diethylzinc in hexane (265 kg, 597 mol) was added at the average rate of 100 L/h via peristaltic pump. The total addition time was 3 h with a target internal temperature of –60±5° C. The solution was then stirred at –65° C. for 45 min. $BF_3.OEt_2$ (2.13 kg, 14.9 mol) was added over 10 min, and the mixture was stirred for 60 min at –65° C. 2-Chloro-5,6-dihydro-7H-cyclopenta[b]pyridin-7-one (25.0 kg, 149 mol) in DCM (250 L, 10V) was added over 3 h via peristaltic pump. The internal temperature was maintained at –65±5° C. The solution was stirred for 1 h at –65° C. The temperature was raised slowly to 14° C. over 13 h. The mixture was transferred to another vessel containing saturated $NH_4Cl$ (20% w/w, 125 L, 5V) initially cooled to 0° C. The internal temperature of the quench was maintained between 10 and 25° C. The mixture was filtered, and the residue was washed with MTBE. The aqueous phase was separated and extracted with MTBE (62.5 L, 2.5V). 125 L $NaHSO_3$ (1% w/w, 5V) was added to the combined organic layers. The mixture was stirred for 30 min and then separated. To the organic layer was added silica gel (30 kg, 1.2 wt) and activated charcoal (2.5 kg). The mixture was stirred for 60 min and then filtered. The filter cake was washed with MTBE (200 L, 8V). The filtrate was concentrated. Recrystallization was conducted as follows: (1) the residue was dissolved in n-heptane (100 L, 4V), (2) the mixture was heated to 60° C. and then slowly cooled to 30° C., (3) a seed crystal of (R)-2-chloro-7-ethyl-6,7-dihydro-5H-cyclopenta[b]pyridin-7-ol (1% wt) was added, and (4) the mixture was cooled slowly to 10° C. and stirred at that temperature for 1 h. The solid was collected by filtration and then triturated with 125 L NaHSO$_3$ (1% w/w, 5V). The slurry was stirred for 1 h and then collected by filtration. The filter cake was washed with water (125 L, 5V) and dried under a flow of N$_2$ for 15 h to afford (R)-2-chloro-7-ethyl-6,7-dihydro-5H-cyclopenta[b]pyridin-7-ol (22.4 kg, 76% yield, 97.3% ee) as a white solid. $^1$H NMR (400 MHz, CDCl$_3$) δ 7.50 (d, J=7.9 Hz, 1H), 7.17 (d, J=8.1 Hz, 1H), 2.99-2.90 (m, 1H), 2.82-2.71 (m, 1H), 2.33 (ddd, J=4.3, 8.7, 13.4 Hz, 1H), 2.19 (ddd, J=6.8, 9.0, 13.5 Hz, 1H), 2.04-1.89 (m, 1H), 1.81 (qd, J=7.3, 14.1 Hz, 1H), 0.94 (t, J=7.5 Hz, 3H); $^{13}$C NMR (101 MHz, CDCl$_3$) δ=166.90, 150.07, 135.67, 134.94, 123.10, 81.98, 36.03, 32.37, 26.47, 8.13. LCMS (APCI) 198.1 [M+H]$^+$.

Example E

Form A of (R)-2-Chloro-7-ethyl-6,7-dihydro-5H-cyclopenta[b]pyridin-7-ol (R)—N-(3-Methyl-1-(pyrrolidin-1-yl)butan-2-yl)-P,P-diphenylphosphinic amide (6.38 kg, 17.9 mol) was suspended in n-heptane (32 L, 3.2V) in a reaction vessel under N$_2$. The suspension was cooled to an internal temperature of −65° C. 1.0 M Diethylzine in heptane (238.7 L, 238.7 mol) was added via peristaltic pump over 2 h. The internal temperature was maintained between −48° C. and −55° C. The solution was then stirred at −65° C. for 45 min. BF$_3$.OEt$_2$ (847 g, 5.97 mol) was added over 15 min, and the mixture was stirred for 60 min at −65° C. 2-Chloro-5,6-dihydro-7H-cyclopenta[b]pyridin-7-one (10 kg, 59.7 mol) in DCM (100 L, 10V) was added over 2 h via peristaltic pump. The internal temperature was maintained at −65±5° C. The solution was stirred for 4 h at −65° C. The temperature was raised slowly to 20° C. over 24 h. The mixture was transferred to another vessel containing saturated NH$_4$Cl (100 L, 10V) initially cooled to −5° C. The internal temperature of the quench was maintained between 10 and 25° C. The mixture was stirred for 30 min and filtered. The residue was washed with DCM (25 L 2.5V), and the layers were separated. The organic phase was washed with water (50 L). The aqueous phase was extracted with DCM (50 L, 5V). The combined organic layers were concentrated. The crude residue was purified by column chromatography (SiO$_2$) with the following petroleum ether:ethyl acetate gradient: (10:1, 200 L), (5:1, 800 L), (1.5:1, 200 L). The eluent was concentrated. The residue was diluted in heptane (10 L, 1V), and the mixture was heated to 60° C. The mixture was cooled slowly to 30° C. and a seed crystal (1% wt) was added. The slurry was cooled to 10° C. and stirred for 1 h. The solid was collected by filtration and dried under a flow of N$_2$ to afford Form A of (R)-2-chloro-7-ethyl-6,7-dihydro-5H-cyclopenta[b]pyridin-7-ol (7 kg, 59% yield, 92.1% ee). The XRPD pattern of Form A is provided in FIG. 1, and a table of some of the XRPD peaks are provided in Table 5.

TABLE 5

| Peak number in spectra | 2θ |
|---|---|
| 5 | 16.19 |
| 9 | 21.00 |
| 12 | 24.18 |
| 13 | 24.88 |
| 14 | 26.54 |

Example F

Form B of (R)-2-Chloro-7-ethyl-6,7-dihydro-5H-cyclopenta[b]pyridin-7-ol (R)—N-(3-Methyl-1-(pyrrolidin-1-yl)butan-2-yl)-P,P-diphenylphosphinic amide (9.57 kg, 26.9 mol) was suspended in hexane (75 L, 5V) in a reaction vessel under N$_2$. The suspension was cooled to an internal temperature of −65° C. 1.0 M Diethylzine in hexane (358 L, 358 mol) was added via peristaltic pump over 2 h. The internal temperature was maintained at −60±5° C. The solution was then stirred at −65° C. for 45 min. BF$_3$.OEt$_2$ (1.27 kg, 8.95 mol) was added over 30 min, and the mixture was stirred for 60 min at −65° C. 2-Chloro-5,6-dihydro-7H-cyclopenta[b]pyridin-7-one (15.0 kg, 89.5 mol) in DCM (150 L, 10V) was added over 3 h via peristaltic pump. The internal temperature was maintained at −65±5° C. The solution was stirred for 1 h at −65° C. The temperature was raised slowly to 20° C. over 17 h. The mixture was transferred to another vessel containing saturated NH$_4$Cl (150 L, 10V) initially cooled to 0° C. The internal temperature of the quench was maintained between 10 and 25° C. The mixture was filtered, and the layers were separated. The aqueous phase was extracted with MTBE (100 L). 75 L NaHSO$_3$ (1% w/w, 5V) was added to the combined organic layers. The mixture was stirred for 30 min and then separated. To the organic layer was added silica gel (30 kg, 2 wt) and activated charcoal (3 kg). The mixture was stirred for 60 min and then filtered. The filter cake was washed with MTBE (120 L, 8V). The filtrate was concentrated, and the residue was dissolved in n-heptane (30 L, 2V). The mixture was heated to 60° C. and then slowly cooled to 30° C. A seed crystal (1% wt) was added. The mixture was cooled slowly to 10° C. and stirred at that temperature for 1 h. The solid was collected by filtration and then triturated with 70 L NaHSO$_3$ (1% w/w, 5V). The slurry was stirred for 2 h and then collected by filtration. The trituration with 1% NaHSO$_3$ was repeated four times. The filter cake was washed with water (45 L, 3V) and dried under a flow of N$_2$ for 3 days to afford Form B of (R)-2-chloro-7-ethyl-6,7-dihydro-5H-cyclopenta[b]pyridin-7-ol (6.76 kg, 38% yield, 99.3% ee) as a white solid. The XRPD pattern of Form B is provided in FIG. 2, and a table of some of the XRPD peaks are provided in Table 6.

TABLE 6

| Peak number in spectra | 2θ |
|---|---|
| 2 | 14.02 |
| 4 | 17.60 |
| 5 | 20.06 |
| 7 | 24.84 |
| 8 | 25.48 |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of preparing a tertiary alcohol, or a salt thereof, comprising combining:
   an optionally substituted phenyl ketone or an optionally substituted pyridinyl ketone, or a salt of any of the foregoing, wherein when the phenyl ketone or pyridinyl ketone is substituted, the phenyl ketone and pyridinyl ketone is substituted with one or more substituents selected from the group consisting of halogen, an unsubstituted $C_{1-4}$ alkyl and an unsubstituted $C_{1-4}$ alkoxy;
   a zinc reagent selected from the group consisting of $Et_2Zn$, $Me_2Zn$ and $Ph_2Zn$;
   a chiral ligand having the structure

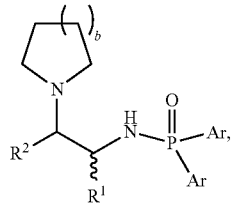

wherein:
   $R^1$ is —$CH_3$, —$CH_2CH_3$, —$CH(CH_3)_2$ or —$C(CH_3)_3$;
   $R_2$ is H; or
   $R^1$ and $R^2$ are taken together along with the carbons to which each $R^1$ and $R^2$ are attached to form an unsubstituted cyclohexyl ring;
   each Ar is independently an unsubstituted or a substituted phenyl or an unsubstituted or a substituted naphthyl, wherein when an Ar is a substituted phenyl or a substituted naphthyl, the phenyl or the naphthyl is substituted with one or more substituents independently selected from the group consisting of halogen, an unsubstituted $C_{1-4}$ alkyl and an unsubstituted $C_{1-4}$ alkoxy; and
   b is 1 or 2; and
   $BF_3 \cdot OEt_2$.

2. The method of claim 1, wherein the optionally substituted phenyl ketone has a structure selected from the group consisting of:

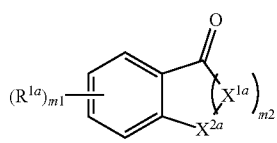
   (A)

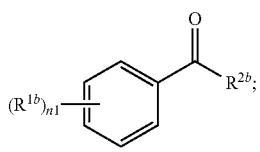
   (B)

wherein:
   m1 is 0, 1, 2, 3 or 4;
   n1 is 0, 1, 2, 3, 4 or 5;
   m2 is 1 or 2;
   $X^{1a}$ is —$CH_2$—;
   $X^{2a}$ is —$CH_2$—, —$CH(CH_3)$—, —$C(CH_3)_2$— or O;
   each $R^{1a}$ and each $R^{1b}$ are independently selected from the group consisting of halogen, an unsubstituted $C_{1-4}$ alkyl and an unsubstituted $C_{1-4}$ alkoxy; and
   $R^{2b}$ is an unsubstituted $C_{1-4}$ alkyl.

3. The method of claim 2, wherein the optionally substituted ketone is selected from the group consisting of:

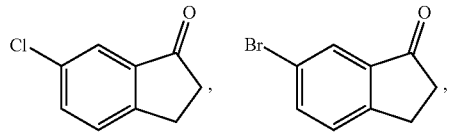

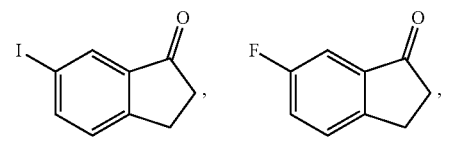

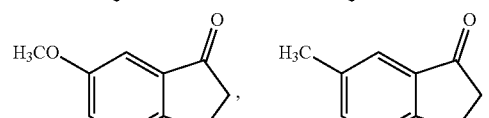

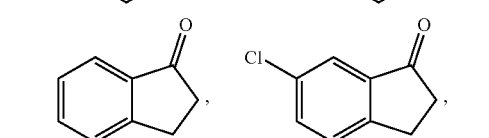

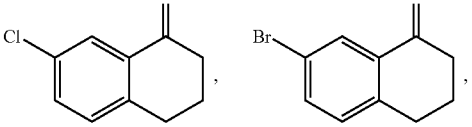

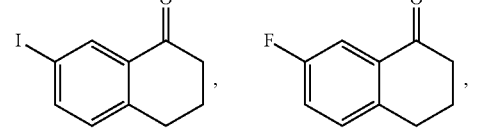

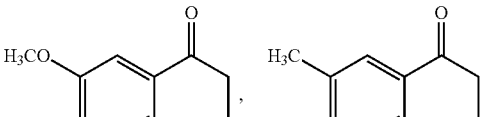

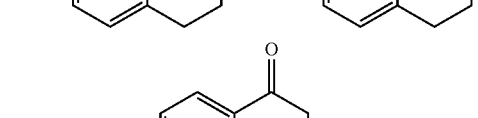

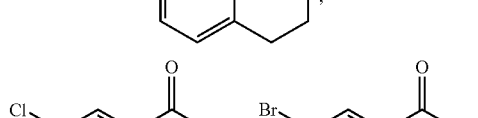

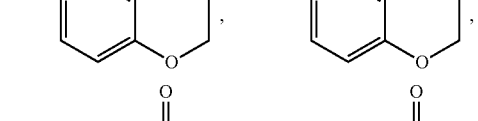

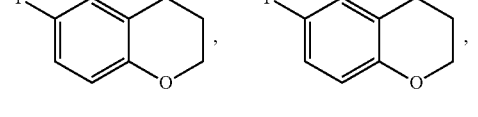

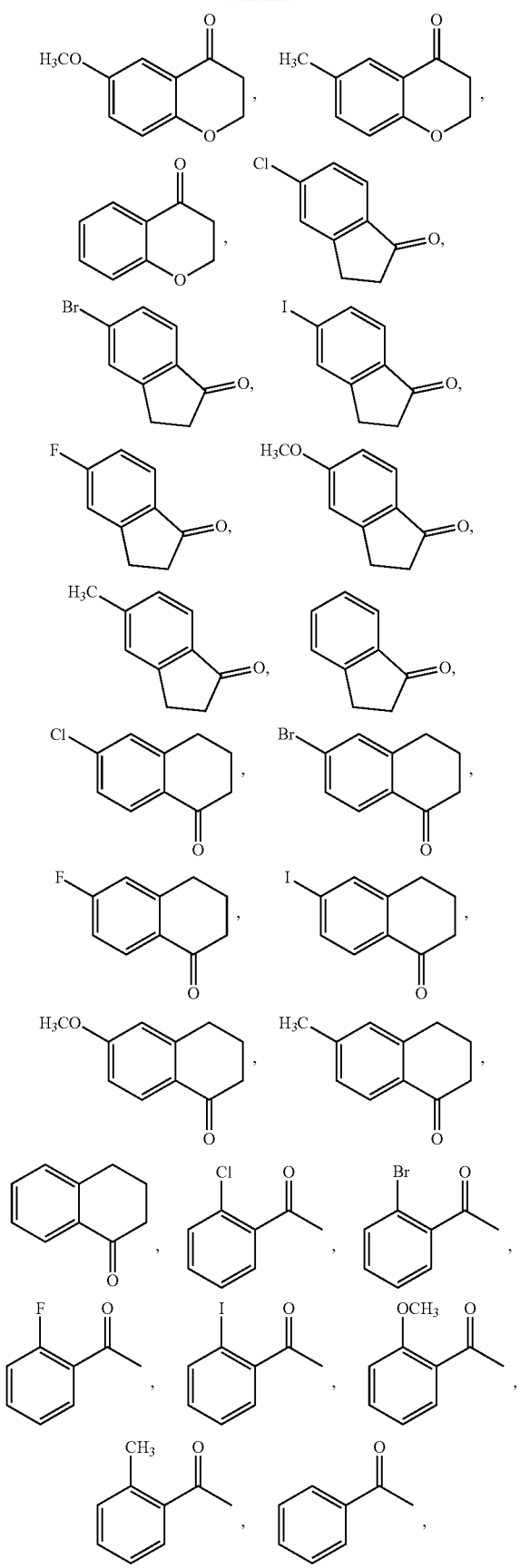

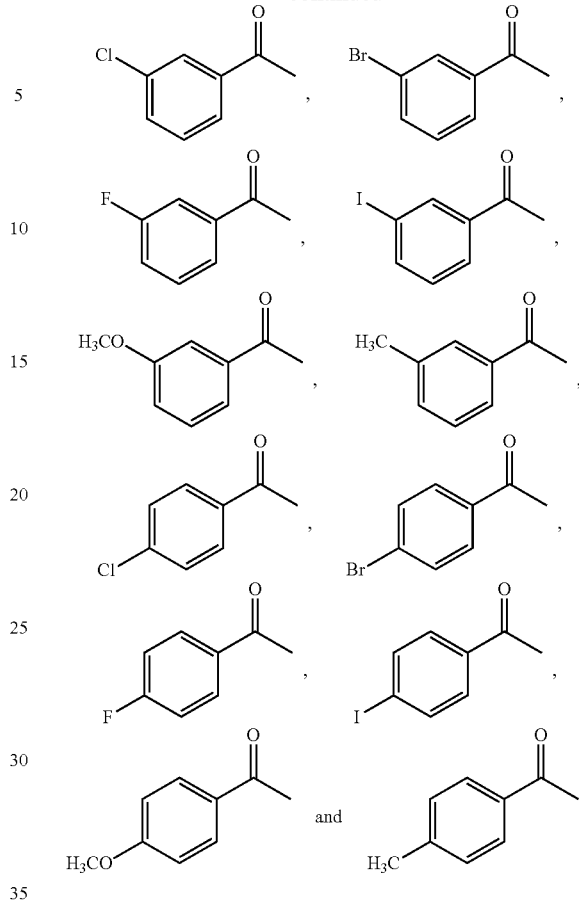

4. The method of claim 1, wherein the tertiary alcohol has a structure selected from the group consisting of:

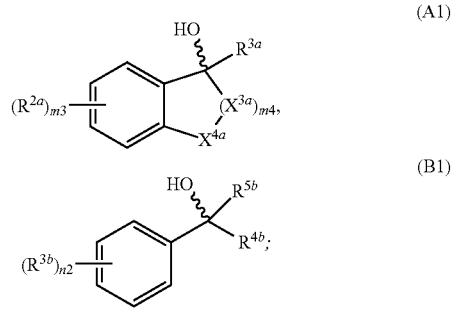

wherein:
m3 is 0, 1, 2, 3 or 4;
n2 is 0, 1, 2, 3, 4 or 5;
m4 is 1 or 2;
$X^{3a}$ is —CH$_2$—;
$X^{4a}$ is —CH$_2$—, —CH(CH$_3$)—, —C(CH$_3$)$_2$— or O;
each $R^{2a}$ and each $R^{3b}$ are independently selected from the group consisting of halogen, an unsubstituted C$_{1-4}$ alkyl and an unsubstituted C$_{1-4}$ alkoxy;
$R^{4b}$ is an unsubstituted C$_{1-4}$ alkyl; and
$R^{3a}$ and $R^{5b}$ are independently —CH$_3$, —CH$_2$CH$_3$ or -Ph.

5. The method of claim 1, wherein the optionally substituted pyridinyl ketone has a structure selected from the group consisting of:

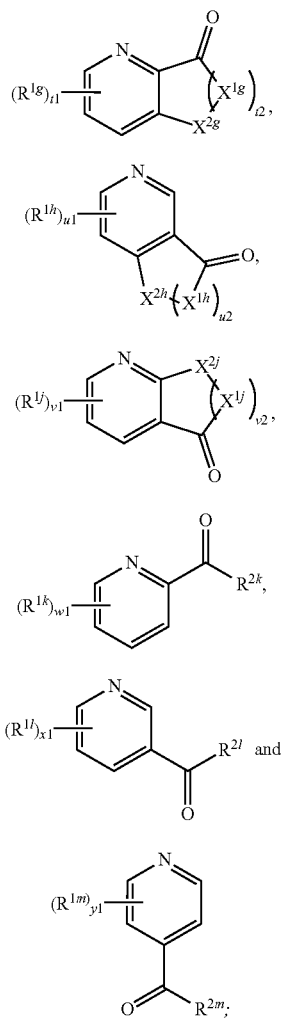

wherein:
t1, u1 and v1 are independently 0, 1, 2 or 3;
w1, x1 and y1 are independently 0, 1, 2, 3 or 4;
t2, u2 and v2 are independently 1 or 2;
$X^{1g}$, $X^{1h}$ and $X^{1j}$ are each —CH$_2$—;
$X^{2g}$, $X^{2h}$ and $X^{2j}$ are independently —CH$_2$—, —CH(CH$_3$)—, —C(CH$_3$)$_2$— or O;
$R^{1g}$, $R^{1h}$, $R^{1j}$, $R^{1k}$, $R^{1l}$ and $R^{1m}$ are independently selected from the group consisting of halogen, an unsubstituted C$_{1-4}$ alkyl and an unsubstituted C$_{1-4}$ alkoxy; and
$R^{2k}$, $R^{2l}$ and $R^{2m}$ are independently an unsubstituted C$_{1-4}$ alkyl.

6. The method of claim 5, wherein the optionally substituted pyridinyl is selected from the group consisting of:

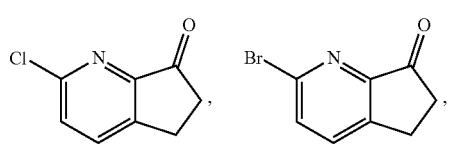

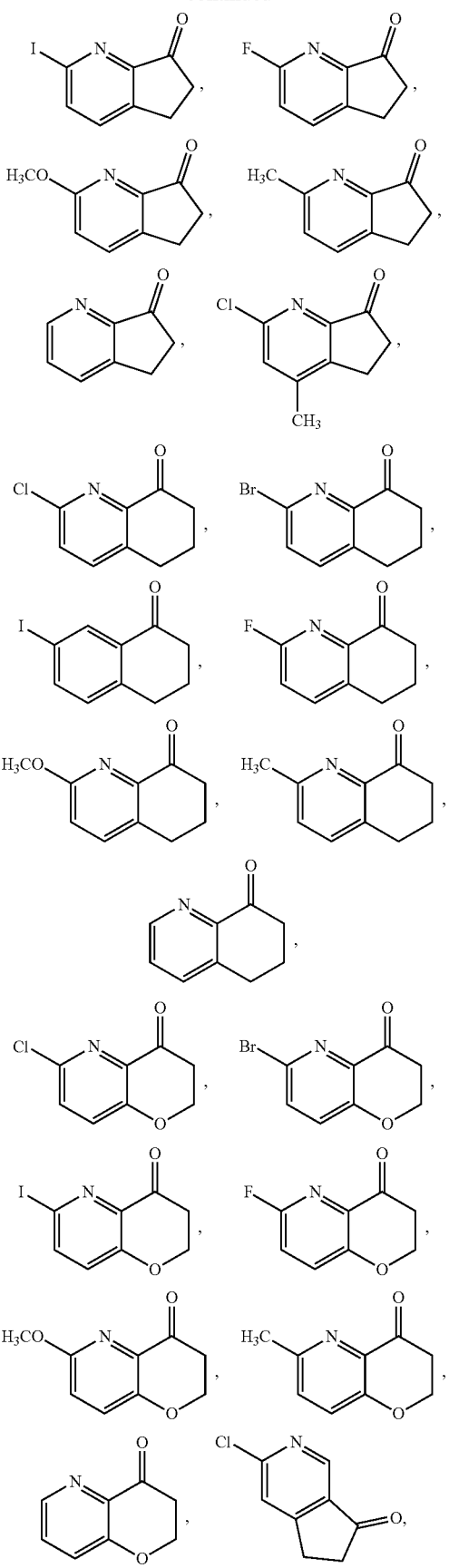

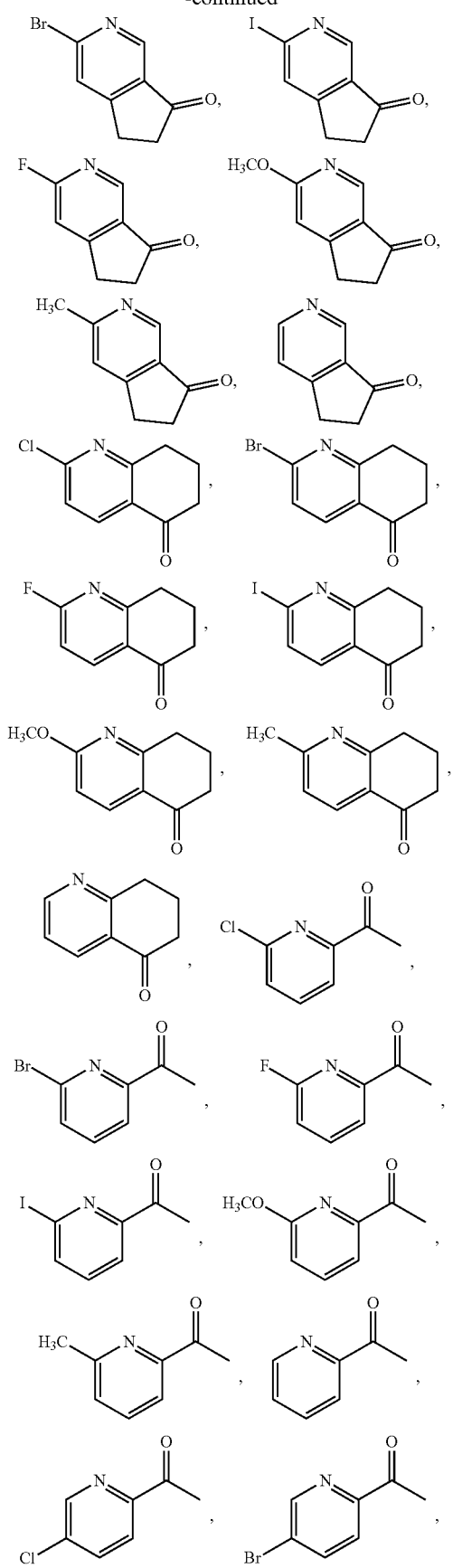
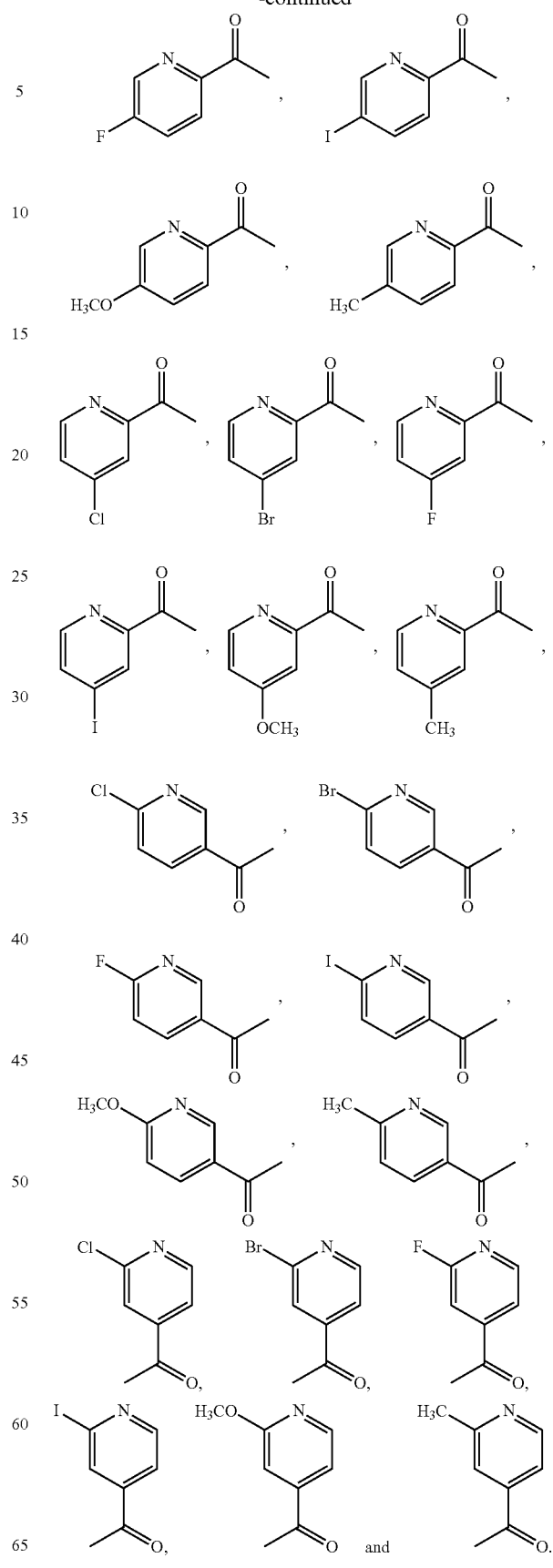

7. The method of claim 1, wherein the tertiary alcohol has a structure selected from the group consisting of:

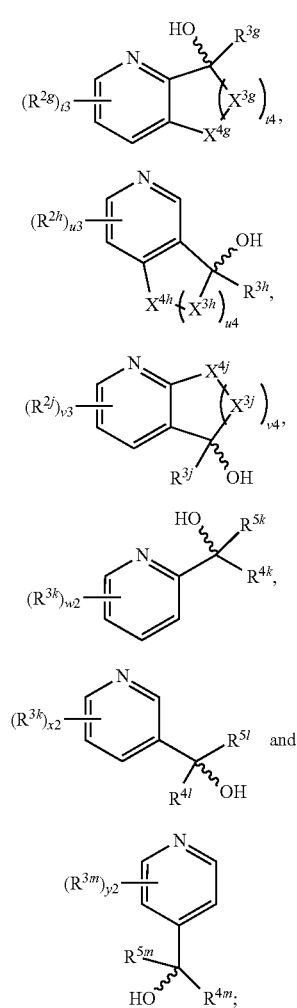

wherein:
t3, u3 and v3 are independently 0, 1, 2 or 3;
w2, x2 and y2 are independently 0, 1, 2, 3 or 4;
t4, u4 and v4 are independently 1 or 2;
$X^{3g}$, $X^{3h}$ and $X^{3j}$ are each —$CH_2$—;
$X^{4g}$, $X^{4h}$ and $X^{4j}$ are independently —$CH_2$—, —CH($CH_3$)—, —C($CH_3$)$_2$— or O;
$R^{2g}$, $R^{2h}$, $R^{2j}$, $R^{3k}$, $R^{3l}$ and $R^{3m}$ are independently selected from the group consisting of halogen, an unsubstituted $C_{1-4}$ alkyl and an unsubstituted $C_{1-4}$ alkoxy;
$R^{4k}$, $R^{4l}$ and $R^{4m}$ are independently an unsubstituted $C_{1-4}$ alkyl; and
$R^{3g}$, $R^{3h}$, $R^{3j}$, $R^{5k}$, $R^{5l}$ and $R^{5m}$ are independently —$CH_3$, —$CH_2CH_3$ or -Ph.

8. The method of claim 1, wherein the tertiary alcohol is obtained in enantiomeric purity of ≥50%.

9. The method of claim 1, wherein the tertiary alcohol is obtained in enantiomeric purity of ≥90%.

10. The method of claim 1, wherein the tertiary alcohol is obtained in enantiomeric purity of ≥95%.

11. The method of claim 1, wherein the chiral ligand has the structure

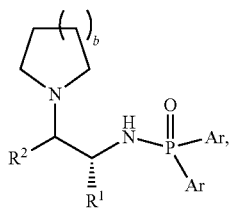

wherein each Ar is an unsubstituted phenyl or a substituted phenyl substituted with one or more substituents independently selected from the group consisting of halogen, an unsubstituted $C_{1-4}$ alkyl and an unsubstituted $C_{1-4}$ alkoxy.

12. The method of claim 1, wherein the chiral ligand has the structure

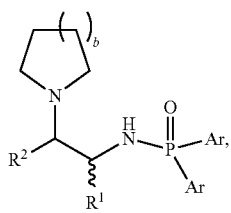

wherein each Ar is an unsubstituted naphthyl.

13. The method of claim 1, wherein the chiral ligand has the structure

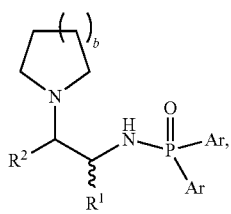

wherein each Ar is a substituted naphthyl substituted with one or more substituents independently selected from the group consisting of halogen, an unsubstituted $C_{1-4}$ alkyl and an unsubstituted $C_{1-4}$ alkoxy.

14. The method of claim 1, wherein b is 1.

15. The method of claim 1, wherein the chiral ligand has a structure selected from the group consisting of

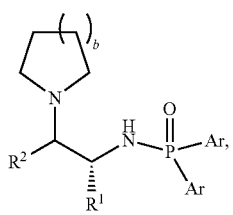 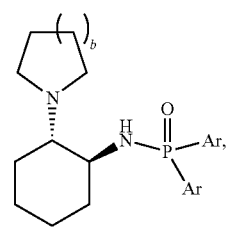

-continued
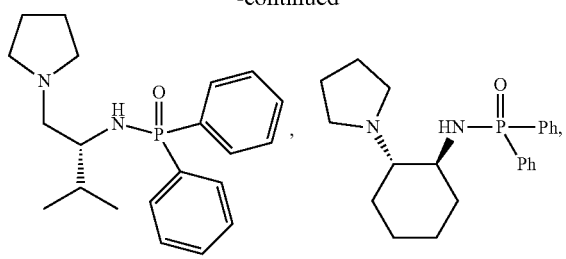
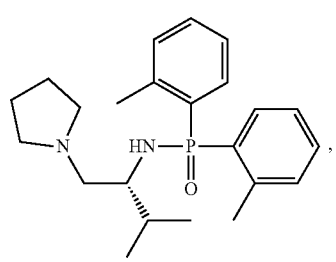
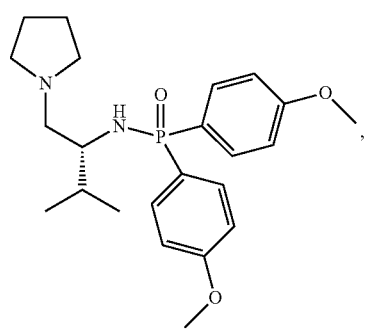
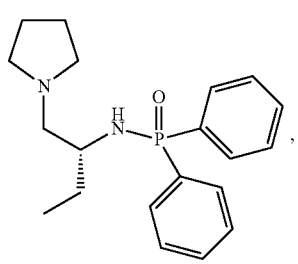
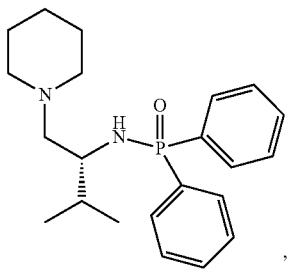
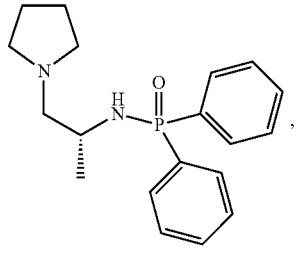
-continued
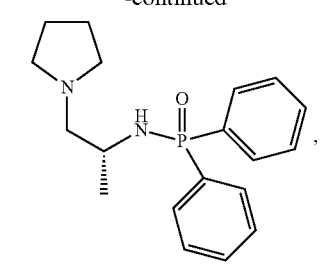
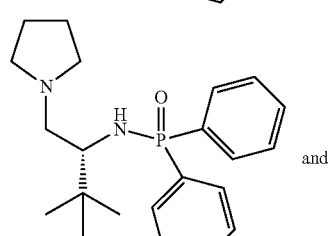 and
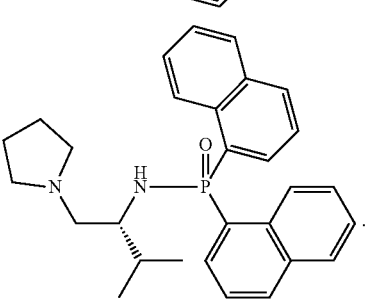.
16. The method of claim 1, wherein the tertiary alcohol is selected from the group consisting of:
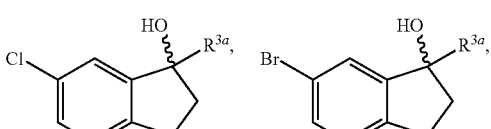
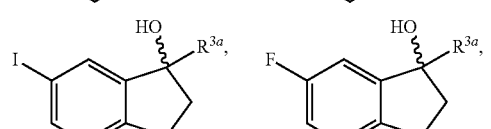
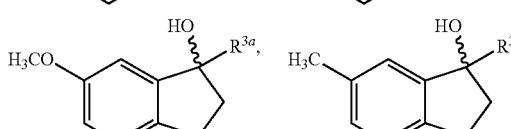
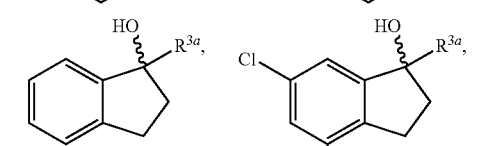
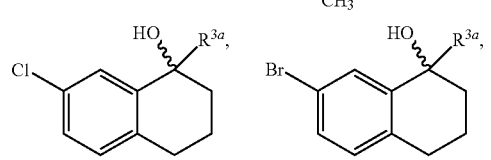

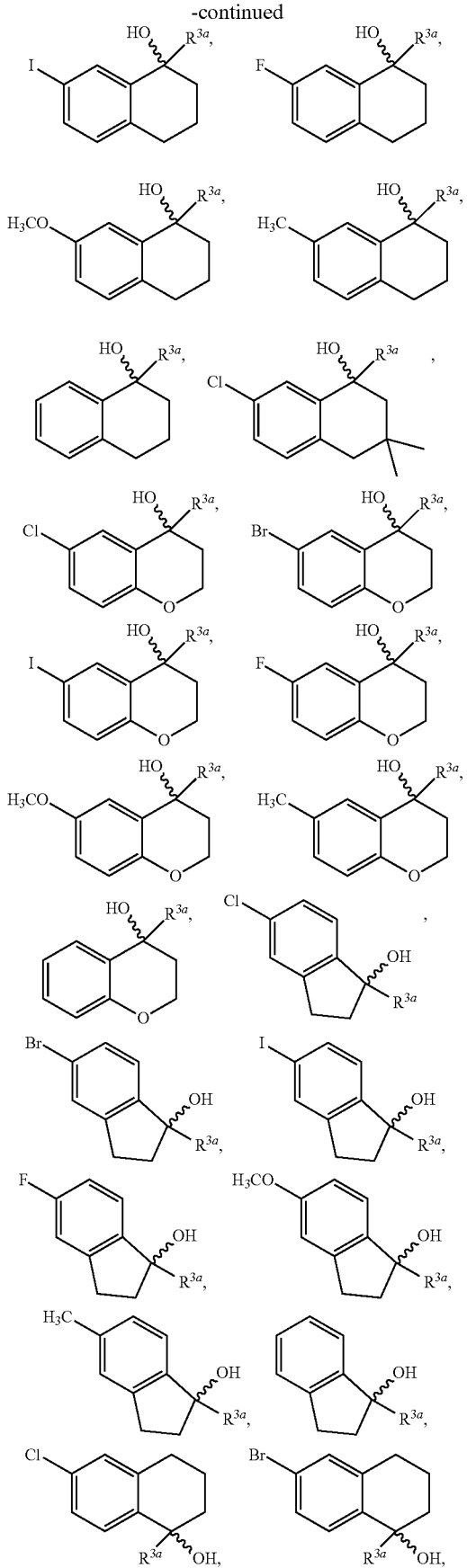
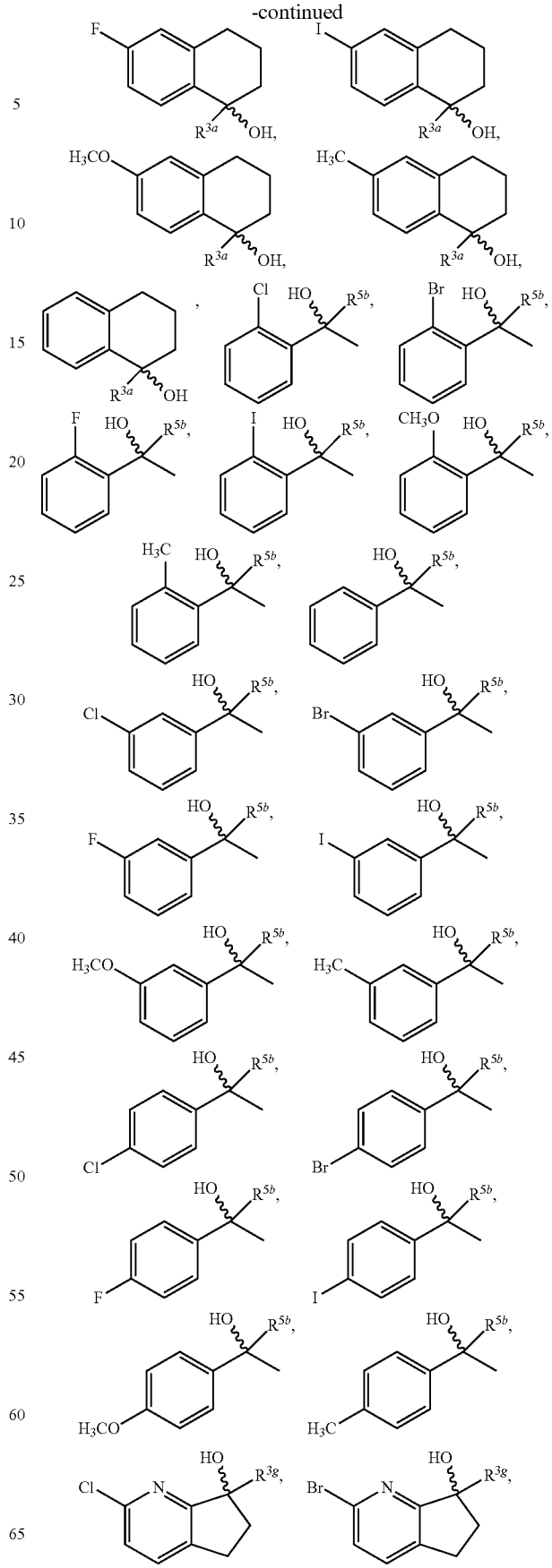

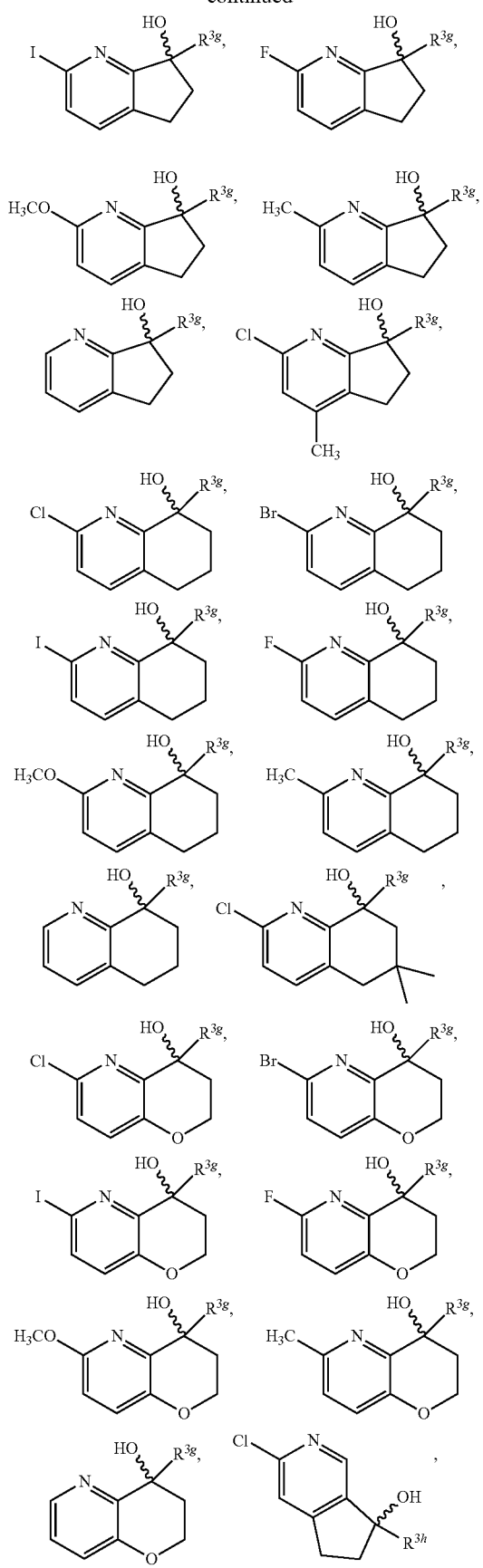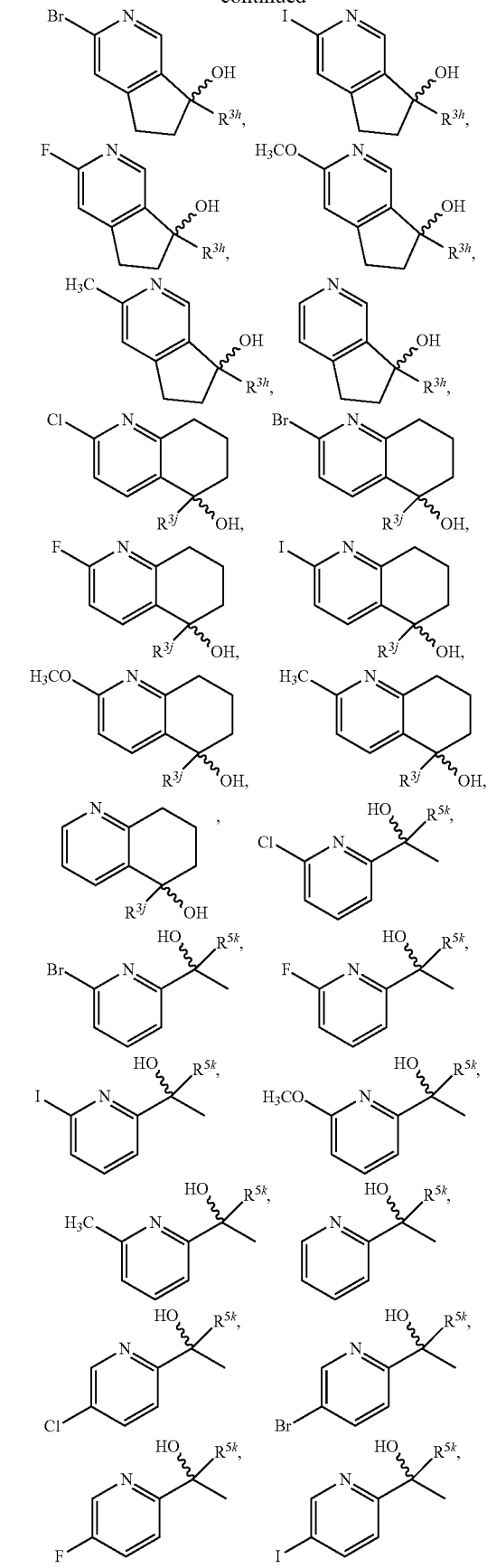

17. The method of claim 1, wherein the tertiary alcohol obtained is selected from the group consisting of:
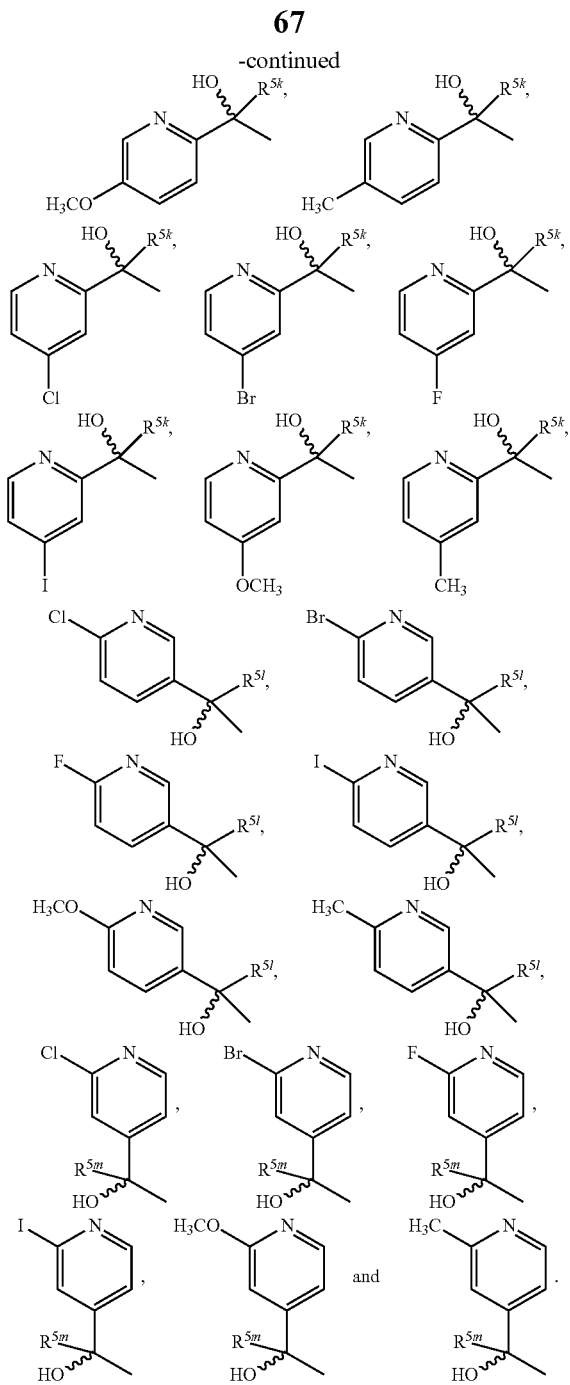
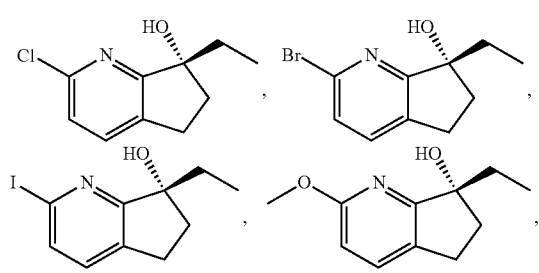
and
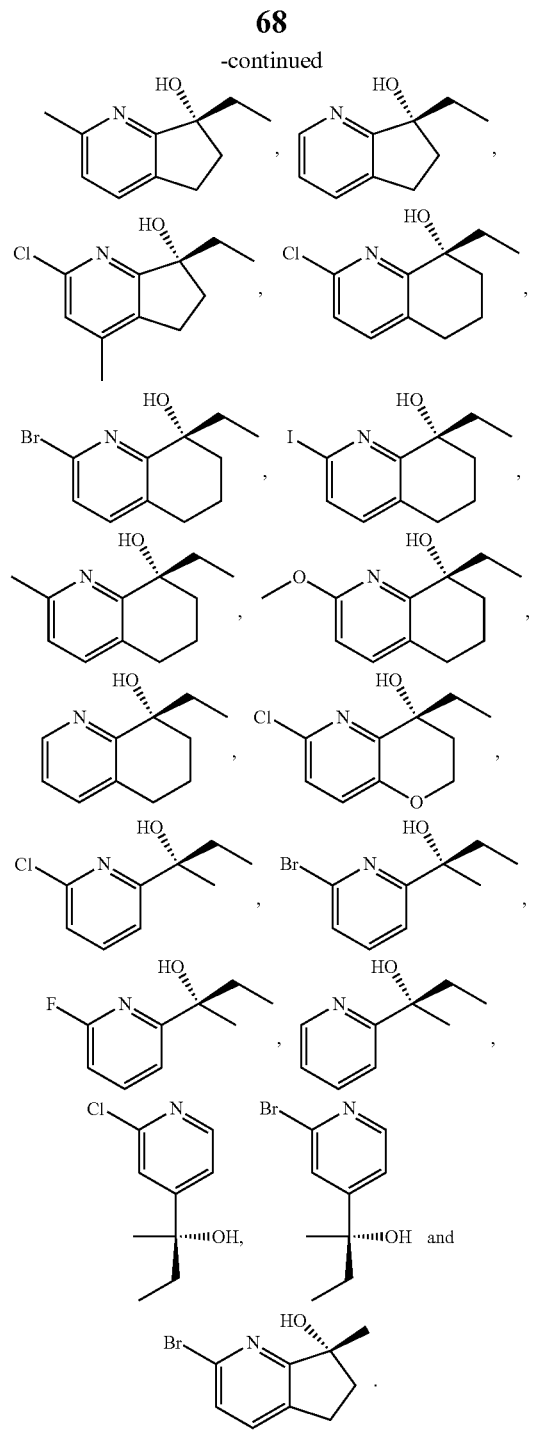
18. The method of claim 1, wherein the method further comprises the use of NaHSO$_3$ on
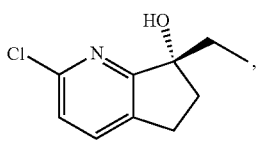
wherein the use of NaHSO$_3$ increases the enantiomeric excess (ee %) of

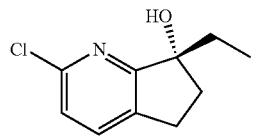
compared to the ee % prior to the use of NaHSO₃.
19. The method of claim 1, wherein the method further comprises recrystallization of
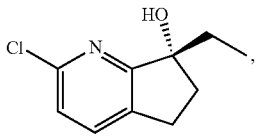
wherein the recrystallization increases the enantiomeric excess (ee %) of
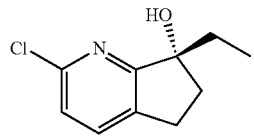
compared to the ee % prior to the recrystallization.
* * * * *